US005536643A

United States Patent [19]
Mock

[11] Patent Number: 5,536,643
[45] Date of Patent: Jul. 16, 1996

[54] NON-RADIOACTIVE METHOD FOR DETERMINING CIRCULATING RED CELL VOLUME, TOTAL BLOOD VOLUME, AND RED CELL SURVIVAL

[75] Inventor: Donald M. Mock, Little Rock, Ark.

[73] Assignee: Board of Trustees of the University of Arkansas, Little Rock, Ark.

[21] Appl. No.: 330,576

[22] Filed: Oct. 27, 1994

[51] Int. Cl.$^6$ ............................................. G01N 33/567
[52] U.S. Cl. .................... 435/7.25; 435/7.5; 435/962; 435/968; 436/63; 436/520
[58] Field of Search .................... 424/1.17; 435/7.25, 435/7.5, 962, 968; 436/520, 63

[56] References Cited

U.S. PATENT DOCUMENTS

| 4,224,942 | 9/1980 | Wu et al. | 210/927 X |
|---|---|---|---|
| 5,122,453 | 6/1992 | Martin et al. | 435/7.24 |

OTHER PUBLICATIONS

S. Albert, "Blood Volume Measurement," in Nuclear Medicine In Vitro, second edtion, B Rothfeld (ed.) (J. B. Lippencott Company 1983) pp. 355–368.

O. Gadeberg et al., "Isolation of Human Peripheral Blood Monocytes: A Comparative Methodological Study," J of Immunol. Methods 31(1):1–10, 1979.

D. Mock, "Sequential Solid Phase Assay for Biotin Based on $^{125}$I–labeled Avidin," in Methods in Enzymology, 184:224–233, 1980.

J. Wormmeester et al., "Immunoselective Cell Separation," in Methods in Enzymology, 184: 314–319, 1990.

"The Measurement of the Total Volume of Red Cells in Man: a Non–radioactive Approach using Biotin," Cavill, et al., British Journal of Haematology, 1988.

"Biotin Labeling of Red Cells in the Measurement of Red Cell Volume in Preterm Infants," Hudson, et al. Pediatric Research, 1990.

"Red Cell Volume and Cardiac Output in Anaemic Preterm Infants", Hudson, et al., Archives of Disease in Childhood, 1990.

"Direct In Vivo Biotinylation of Erythrocytes as an Assay for Red Cell Survival Studies,"Hoffman–Fezer, et al., Annals of Hematology, 1991.

Primary Examiner—Carol A. Spiegel
Attorney, Agent, or Firm—Ray F. Cox, Jr.

[57] ABSTRACT

A method for the non-radioactive determination of circulating red cell volume, total blood volume and red cell survival. Red blood cells are biotinylated and injected into the subject for dilution in the subjects total blood volume. A diluted sample is extracted and incubated with a label, either a radionuclide or a fluorescent moiety complexed with avidin or streptavidin. Detection of the label, as for example by gamma counting in the case of a radionuclide or fluorescence activated cell sorting in the case of a fluorescent moiety, allows calculation of the red cell volume and therefrom, total blood volume. Sequential measurements are possible with this method. Aspects of the method include enhanced biotin labeling and separation of cells by density gradient means.

6 Claims, 12 Drawing Sheets

DECLINE IN $^{14}$C-CYANATE LABELED RBC WITH TIME

SURVIVAL OF $^{14}$C-CYANATE LABEL: LATER STUDIES

COMPARISON OF RBC VOLUME RESULTS:
BIOTIN VERSUS $^{51}$CR

COMPARISON OF RBC VOLUME RESULTS:
BIOTIN VERSUS $^{14}$C-CYANATE

FIG. 15    DILUTION OF INFUSATE WITH UNLABELED CELLS
% Positive Determined by FACS vs. % Positive by Dilution
Corrected for % False Positive
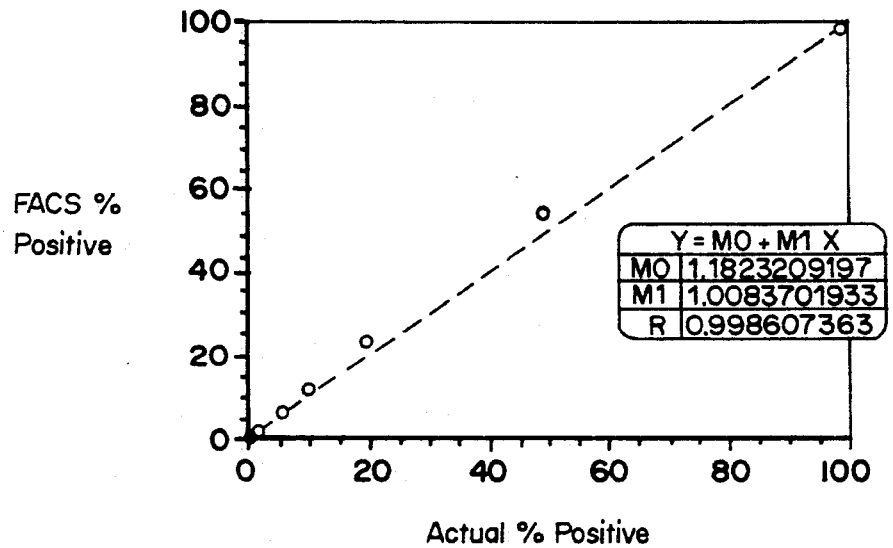
FIG. 16    DILUTION OF INFUSATE WITH UNLABELED CELLS
% Positive Determined by FACS vs. % Positive by Dilution
Corrected for False Positive
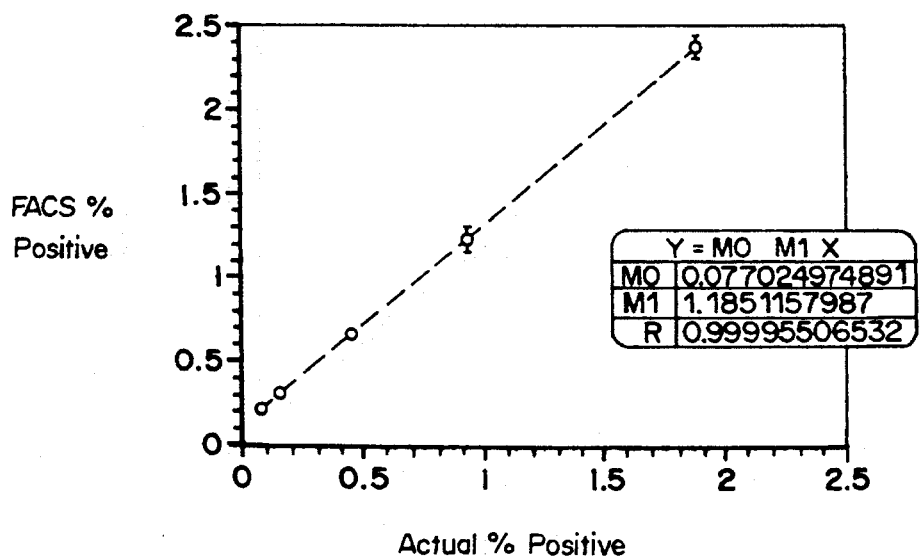

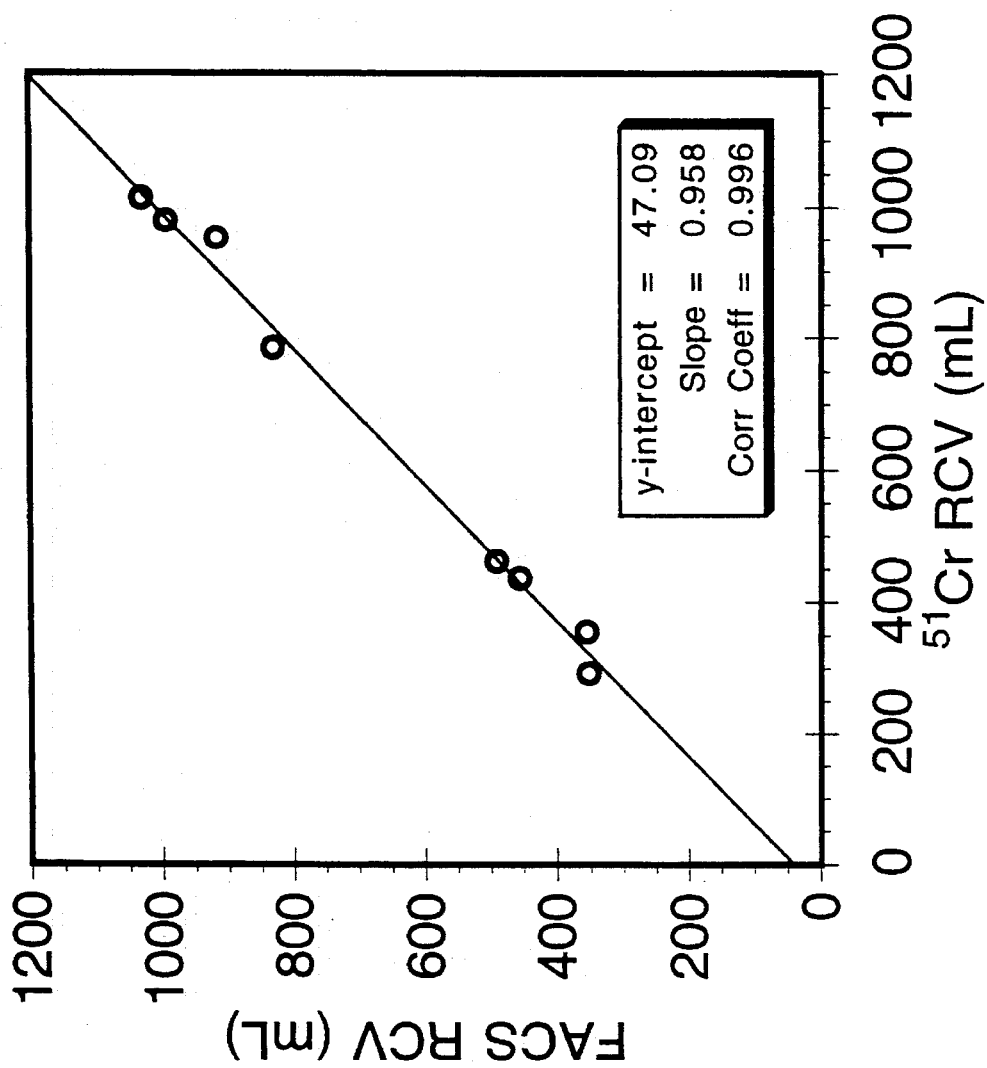
Figure 16A. Red Cell Volume Comparison FACS vs. $^{51}$Cr

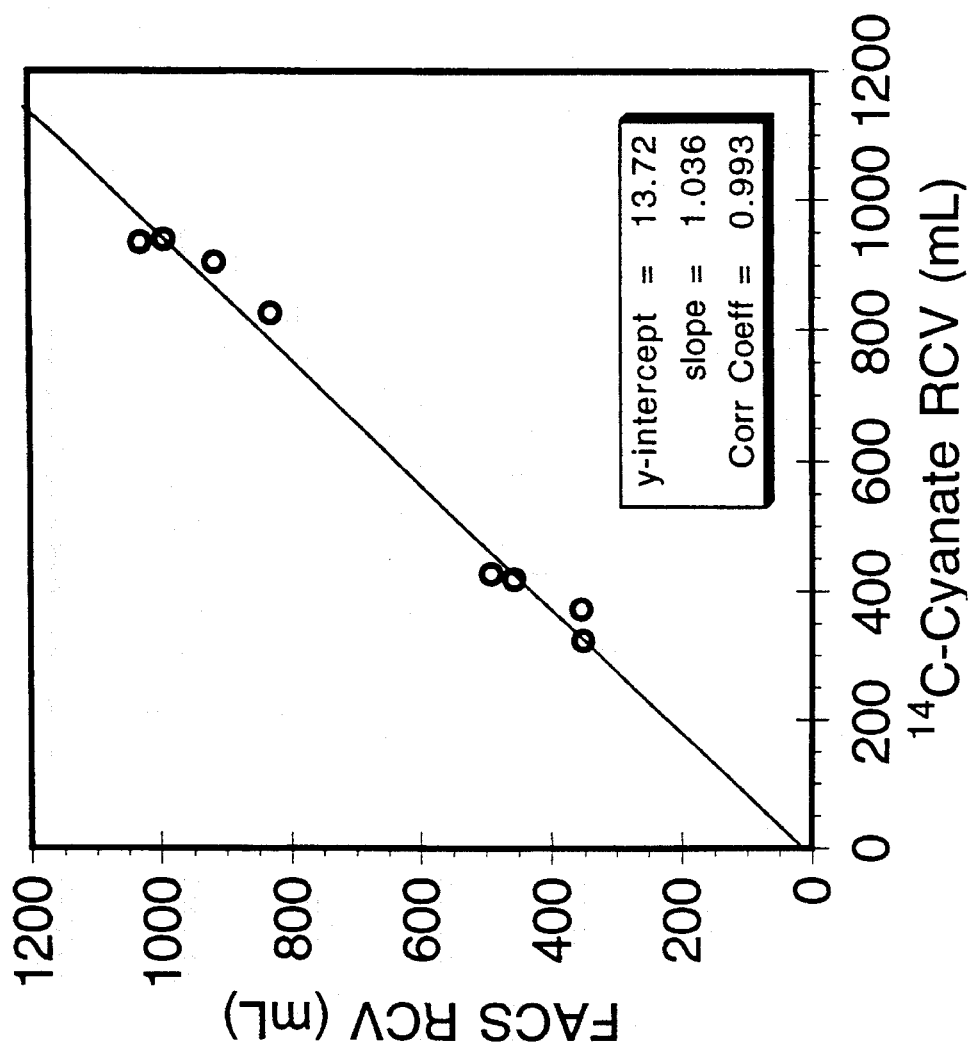
Figure 16B. Red Cell Volume Comparison FACS vs. $^{14}$C-Cyanate

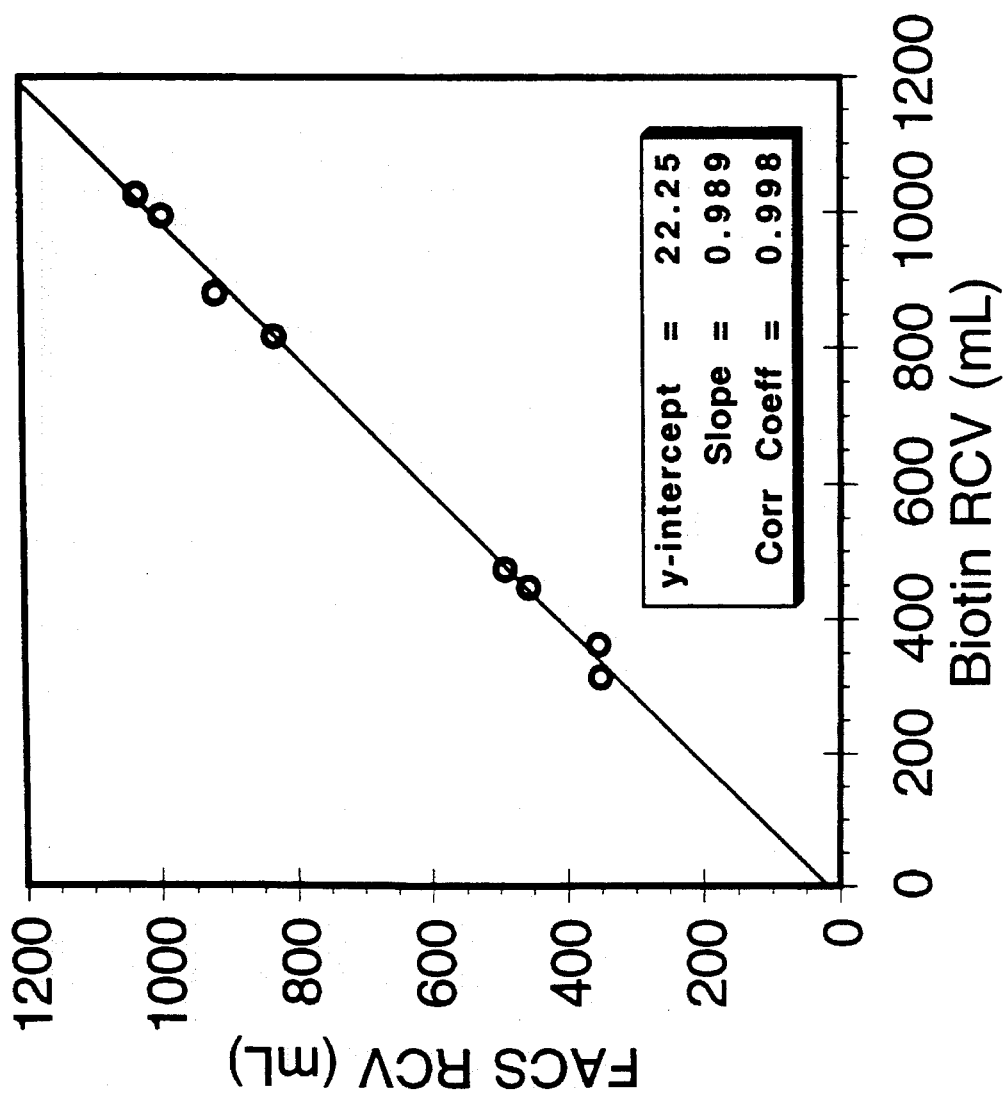
Figure 16C. Red Cell Volume Comparison FACS vs. Biotin Method

NON-RADIOACTIVE METHOD FOR DETERMINING CIRCULATING RED CELL VOLUME, TOTAL BLOOD VOLUME, AND RED CELL SURVIVAL

BACKGROUND OF THE INVENTION

The present invention relates to methods that will allow the measurement of total circulating red cell volume, total blood volume and red cell survival, and, in particular, to making such measurements without exposing the subject to radiation. This invention allows multiple measurements in the same individual over clinically meaningful periods of time (e.g., 72 hours). The process requires only readily available equipment, such as a gamma counter. The process is sensitive enough for potential application even to a low birth weight infant or fetus.

All methods for measuring red cell volume in common use depend upon the measurement of the initial dilution of erythrocytes, or red blood cells, labeled with one of a variety of tracers, such as radionuclides. Typically, a volume of blood is drawn from the subject, the red blood cells are labeled with a tracer, and reinjected into the subject where they are diluted in the entire volume of the subject's blood. At a later time, one or more samples of blood are withdrawn and the labeled blood cells are quantified. A straightforward calculation then yields the total volume of red blood cells. Likewise, total blood volume may be calculated from the red cell volume and hematocrit.

Commonly the tracer used to label the red blood cells is a radionuclide. The standard radionuclide used is $^{51}Cr$ because the red cell binding properties of chromium are excellent, though not perfect. Other radionuclides have also been investigated as red cell tracers; these nuclides include $^{99M}Tc$ and $^{111}In$. These two radionuclides have the desirable characteristic of short half-lives leading to reduced radiation exposure; however, these same short half-lives mandate a readily available supply and predictable timing for the use of the radionuclide. Each of these elements has its own special problems in conversion to chemical forms that will bind firmly to red cells. Short half lives also complicate and limit the measurement of red cell survival.

The special binding properties of chromium have been explored in an attempt to develop a practical, nonradioactive method for determination of red cell volume. One method uses $^{50}Cr$, a stable isotope of chromium, with subsequent neutron activation. Another uses $^{52}Cr$, the abundant stable chromium isotope, with atomic absorption analysis. A third uses cesium with subsequent analysis of x-ray stimulated fluorescence. Each of these methods requires highly specialized equipment: either 1) a neutron source, 2) a Zeeman electrothermal atomic absorption spectrometer, or 3) an $^{247}Americium$ source and highly sensitive 1024-channel silicon detector.

Plasma volume can be measured based on the dilution of labeled albumin or dyes that bind to albumin such as Evan's blue dye; blood volume and red cell volume can then be calculated from the hematocrit; i.e., the volume after centrifugation of the cellular elements of blood in relation to the total volume. The dye methods and albumin methods both measure the albumin space and are limited by the same problems with capillary permeability. Dye dilution methods do not yield reproducible results due to variability between individuals in both mixing time and loss from circulation. These estimates are further confounded in situations of increased capillary permeability such as thermal burn, sepsis, and prematurity; in such situations, the albumin distribution volume can substantially exceed the true plasma volume.

Red cell volume can be measured once using $^{51}Cr$ labeling of autologous red cells, and total blood volume can be calculated from the hematocrit. For serial measurements, which are necessary, for example, to calculate red cell survival, one must roughly double the dose of $^{51}Cr$ with each successive measurement in order to produce a meaningful increment over the residual $^{51}Cr$ left in the blood from the previous measurements. Thus, serial measurements result in increasing exposure to radioactivity. This problem appears to render multiple blood volume assessments by the $^5Cr$ method impractical; indeed, a clinical application of the type proposed here has not been published despite the fact that $^5Cr$ has been an established red cell label for more than 20 years.

Biotin is a water-soluble vitamin generally classified in the B group. A number of biotin-binding proteins are known, but avidin and streptavidin are two proteins with very high binding affinities for biotin. One is found in egg white, and the other in the secretions of the mold *Streptomyces avidini*. In the natural setting, both probably act as antimicrobials by preventing microbes from obtaining biotin. The equilibrium binding constant of biotin for avidin (and of biotin for streptavidin) is $10^{15}$ $M^{-1}$. This extraordinarily large binding constant, as well as the large association rate constant and small dissociation rate constant, dictate that the binding is very rapid and essentially irreversible. Binding is highly specific with respect to the structure of the biotin bicyclic ring and is promoted by the hydrophobic binding pocket of avidin. This binding specificity has rendered the biotin:avidin interaction highly resistant to interference by substances such as antibiotics and chemotherapeutic agents that are often present in the plasma of individuals in clinical situations. This unusually strong and specific binding has been used for a variety of applications, including ones that use plasma from patients in many clinical settings.

The biotin:avidin interaction has already been used to measure red cell volume in normal adults, I. Cavill, et al., "The Measurement of the Total Volume of Red Cells in Man: A Nonradioactive Approach using Biotin," British Journal of Haematology, 1988, and in neonates, I. R. B. Hudson, et al., "Biotin Labeling of Red Cells in the Measurement of Red Cell Volume in Preterm Infants," Pediatric Research, 1990 Those studies found a close agreement for the red cell volume by the nonradioactive method with values from the standard $^{51}Cr$ method. However, the label disappeared within seven days, making measurements of red cell survival impossible and potentially making repetitive measurements of red cell volume very complicated. In addition, the method depended upon the use of a fluorescence activated cell sorter (FACS). These machines are increasingly available in tertiary medical centers and should not be considered highly specialized equipment; however, the method of the present invention uses either a simplified system for detecting the nonradioactive label that requires only a gamma counter and a centrifuge or a FACS technique that yields accuracy not applied previously to this problem. This technique for labeling and FACS detection is novel in the accuracy attained and allows sequential RCV measurements and red cell survival measurements that have not been reported before.

An additional related clinical application has similar potential for broad application—the determination of blood volume in trauma patients arriving in the emergency room. Information about extent of bleeding prior to arriving in the emergency room could potentially be available within one hour using the FACS technology of the present invention and might be life saving. Any delay needed for washing and labeling the cells could be avoided by preparing and storing "universal donor" red cells ahead of time. Prior preparation is feasible because the labeling technique described herein produces a stable label when stored in the modern red cell storage media at 4° C. These universal donor labeled red cells could be stored up to the FDA mandated limit (e.g., 35 days or 42 days).

Circulating red cell volume, or simply, red cell volume (RCV) is used herein to designate the total volume of circulating red cells. Oxygen carrying capacity is directly proportional to total circulating hemoglobin; total circulating hemoglobin can be calculated from the product of the circulating red cell volume and the mean corpuscular hemoglobin concentration. Total blood volume can be calculated from the red cell volume and the hematocrit (with corrections for trapped plasma and for the difference between peripheral and central hematocrit).

Red cell survival (RCS) is defined as the percentage of transfused red cells that remain in circulation at a given point in time. To a first approximation, red cells are removed in two phases; the early "rapid removal" phase and the remaining "slow removal" phase. By implication, there must be at least two populations of cells. The first consists of cells that are damaged and are removed from circulation rapidly after transfusion. The percent survival at 24 hours after transfusion ("post-transfusion recovery") reflects this population. The second consists of cells that are damaged minimally, if at all, and are slowly removed from circulation. The time loss of 50% of the label ($T_{50}$) is a commonly used parameter and reflects primarily this population; the $T_{50}$ can be calculated from the first order decay constant assuming monoexponential disappearance. The average potential life span can be determined directly or as the time to greater than 95% disappearance of the label. These parameters are measures of the slow removal phase.

In critically ill patients care, invasive monitoring and sophisticated electronic technology have enabled the clinician to determine the cardiac output, filling pressures of the right and left side of the heart, mean pulmonary and arterial pressures, and pulmonary and peripheral vascular resistance. These advances have led to a great increase in our ability to manipulate central hemodynamics, modify cardiac activity, minimize cardiac work, and maximize cardiac output. These measurements have also given us insight into and understanding of the hemodynamic changes associated with endotoxemia and shock. A critical capability that remains unavailable is accurate serial assessment of red cell volume and total blood volume. During management of major trauma, total blood volume may vary widely among individuals and in a single individual. These changes in blood volume can have major effects on central hemodynamics and, in turn, on oxygen delivery, extraction, and consumption.

If one were able to accurately and repetitively measure red cell volume and total blood volume, then resuscitation and pharmacological management of complex patients suffering from severe sepsis or hypovolemic shock of any etiology would be enhanced because accurate values for true blood loss and true blood volume would be available serially in each patient, moreover, this information would be available hours before the body's homeostatic mechanisms compensate for the blood loss by expanding the plasma volume and producing the attendant decrease in hematocrit and hemoglobin concentration. For example, adults who are burn treatment inpatients undergo clinically indicated procedures for closure of their burn wounds. Burn wound closure procedures can result in large volume blood losses. Typical blood loss estimates are between 50 cc to 150 cc of blood loss for each 1% of the patient's body surface are that must have the burn wound excised and skin grafted. Therefore, excision and grating of a 20% body surface area burn in a 70 kg adult male can result in a blood loss of 1,000–3,000 cc. This loss occurs over about one hour. Assuming a blood volume of 5,000 cc, this would represent an acute loss of 20%–60% of total blood volume. Currently intra- and peri-operative blood loss is estimated by a gross subjective examination of blood on discarded sponges and drapes. Current clinical estimates of circulating blood volume in the perioperative and postoperative patient include indirect findings such as blood pressure, pulse, urine output, the acid-base balance, extremity temperature, and skin color. Serial measurements of hemoglobin and hematocrit can also be used to estimate blood volume but actually reflect the red blood cell concentration rather than red blood cell volume. The ability to accurately determine circulating red cell volume and blood volume several times during critical periods would greatly aid in the care of the unstable and hypovolemic patient by accurately dictating red blood cell and crystalloid transfusion requirements for replacement of losses. Unfortunately, repetitive measurements are not currently feasible using available methods for the technical reasons discussed above.

Premature infants are among the most heavily transfused of all patient groups. Of the 38,000 premature neonates with birth weight greater than 1500 g who are born each year in the United States, about 80% require multiple red cell transfusions; many of these infants receive cumulative transfusion volumes in excess of their total blood volume. Multiply-transfused infants may be exposed to two to eighteen different donors. Concerns about transfusion-related disease have not caused a striking reduction in blood utilization by these infants because the transfusions are perceived to be necessary.

Despite the fact that neonatal transfusions consume important amounts of health care resources and are associated with increased risk of morbidity and mortality, the scientific basis for most neonatal transfusion practices is considerably weaker than the basis for transfusion practices in adults. An important limitation in knowledge about neonatal anemia is the inability to measure red cell survival and blood volume because current methods expose the infant to unacceptable doses of radiation.

The idea that the portion of the infant's blood retained in the placenta (so called "cord blood") could be harvested and provided to the infant at a later time has attracted attention recently. In theory, use of these autologous red cells would minimize transfusion transmitted disease. However, knowledge of the storage characteristics of this fetal blood is quite limited. In order to assess the efficacy of storage, measurement of the survival of the transfused red cells is required. However, current practical methods are precluded by the required radiation exposure.

There is also a need for a nonradioactive method for red cell volume of the pregnant woman and the fetus. Changes in red cell volume and blood volume have been hypothesized to have pathogenic roles and prognostic value in toxemia of pregnancy, gestational diabetes, and gestational exacerbation of connective tissue disease for the mother, and in intrauterine growth retardation and hydrops secondary to immune, infectious, and cardiac causes for the fetus. $^{51}$Cr measurements are precluded and, as discussed below, measurements of red cell and vascular volume by alternative methods are impractical or unsatisfactory.

The problems and disadvantages of the prior art methods and the significant advantages of a non-radioactive method of determining red cell and blood volume and red cell survival as described above are addressed by the method of the present invention. This method builds on the method originally reported by Cavil, et al. that suggested biotinylation of red blood cells and subsequent incubation in florescinated streptavidin would allow quantitation of the red blood cell's dilution in vivo using florescence activated cell sorting (FACS). The present invention also utilizes biotinylated red blood cells but with significant enhancements. The biotin label is firmly attached allowing more accurate determination of the red cell volume and blood volume. One detection system of the present invention uses $^{25}$I-Streptavidin and gamma counting as a detection system. Rather than being bound to the red blood cells injected into the patient, the radionuclide (complexed with streptavidin or other biotin-binding protein) in the present process is bound to the biotinylated red blood cells after the second volume of blood containing the diluted biotinylated cells is withdrawn from the patient. The method of the present invention is also enhanced by separation of red blood cells from other types of blood cells and plasma components using a density gradient. Thus the technology is more practical. The accuracy of the method has been demonstrated in vivo and has the capability of measuring survival red blood cells after transfusion as well—a capability not available using the method of Cavil, et al. As disclosed herein, we have made two important breakthroughs in the use of FACS technology in this application. These breakthroughs have enabled highly accurate measurements of red cell volume and red cell survival that permit completely new applications such as sequential measurement of red cell volume. A concept of using this method for multiple measurements of blood cell volume on clinically meaningful time intervals for use in measuring trauma blood loss in trauma patients is also disclosed.

BRIEF DESCRIPTION OF THE DRAWINGS

The invention as exemplified by the preferred embodiments is described with reference to the following drawings in which:

FIG. 15 is a graph showing dilution of infusate with unlabeled cells: % positive determined by FACS versus % positive by dilution.

FIG. 16 is a graph showing dilution of infusate with unlabeled cells: % positive determined by FACS versus % positive by dilution.

FIG. 16A is a red cell volume comparison of FACS versus $^{51}$Cr.

FIG. 16B is a red cell volume comparison of FACS versus $^{14}$C-Cyanate.

FIG. 16C is a red cell volume comparison of FACS versus Biotin Method.

DETAILED DESCRIPTION OF THE PREFERRED EMBODIMENTS

Red cells from either humans or sheep are washed and biotinylated. A series of N-hydroxysuccinimide biotinylating agents (e.g. NHS-biotin) have been evaluated as labeling agents from human and sheep red cells. High specific activity $^{125}$I-streptavidin was used to measure biotinylating density per volume of blood and per cell. Density gradient centrifugation is used to separate bound from free $^{125}$I-streptavidin. Gamma counting is used for the detection of bound $^{125}$I-streptavidin. Damage from biotinylation was assessed in vitro by measuring release of K+, LDH, and hemoglobin.

Figure 17:
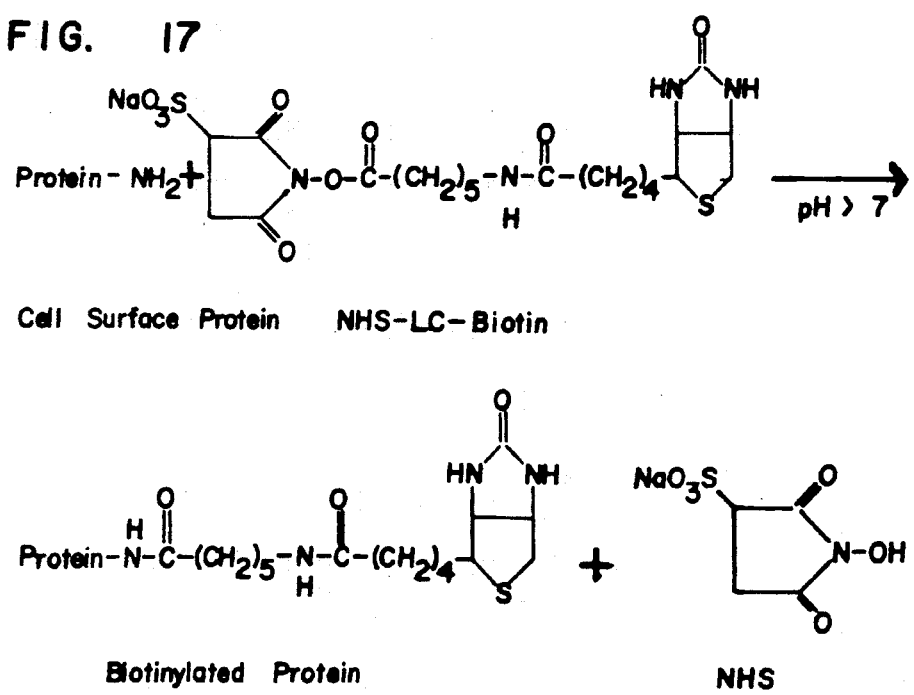
FIG. 17 is a diagram of the biotinylation reaction for N-hydroxysuccinimide-long chain-biotin.

Initially, we used "long chain" biotin. Depicted in FIG. 17 is the biotinylation reaction for N-hydroxysuccinimide-long chain-biotin (NHS-LC-biotin). In the nomenclature of organic chemistry, the compound is sulfosuccinimidyl 6-(biotinamide) hexanoate. A sulfonate group is attached to NHS to promote water solubility; thus, technically, this compound is really sulfo-NHS-LC-biotin, but it is commonly referred to as NHS-LC-biotin. The reaction occurs by nucleophilic attack of an amine (e.g., the e-amino group of a lysine residue) towards the NHS ester.

The reaction results in a stable covalent amide bond to proteins in the outer surface of the RBC membrane and the release of N-hydroxysuccinimide as a by-product which is washed away.

Figure 18:
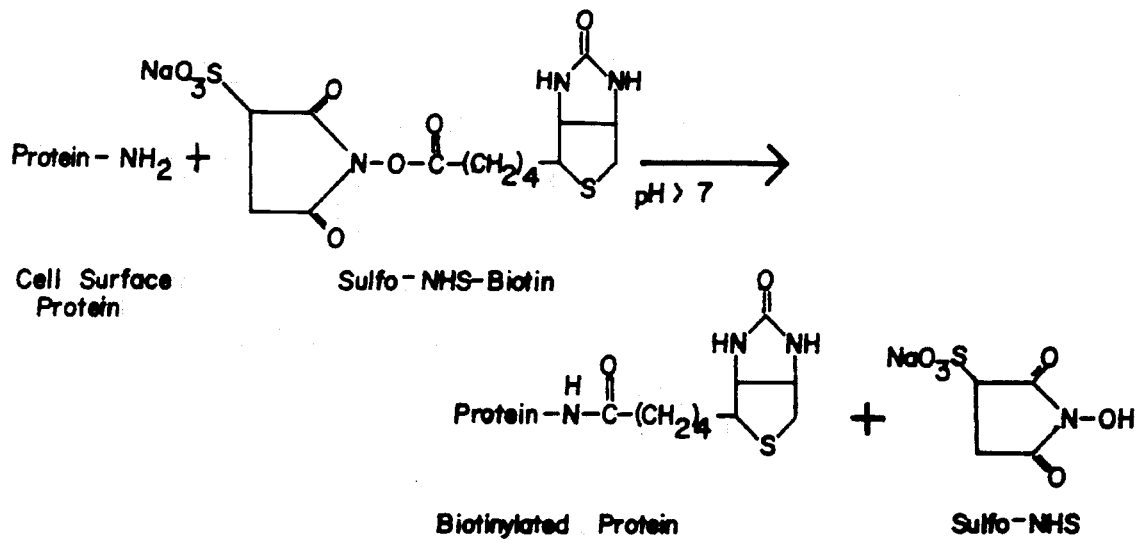
FIG. 18 is a diagram of the labeling reaction for sulfo-NHS-biotin.

Depicted in FIG. 18 is the labeling reaction for sulfo-NSH-biotin; this "short chain" label was also investigated. Unless otherwise specified, biotin is used herein to refer to any form of biotin. "Short-chain" biotinylating agent has been chosen for the initial human applications.

In alternative embodiments of the present method, we also include the use of fluorescence activated cell sorting (FACS) as a detection system. FACS has the advantages of requiring very low sample volumes from the subject and rapid analysis time.

Although FACS was used as the detection system by Cavil, et. al., we have made technical and conceptual break-throughs in the application of FACS technology to this process that make our application distinct and novel. Those applications include the following:

1) A stable label leads to a discrete population of cells as detected by FACS. This in turn allows much more precise quantitation of both red cell volume and red cell survival.

2) As described in more detail below, there is inherent nonlinearity in the FACS machines available to us and probably in most FACS machines available to clinical facilities. As part of the process, we have developed a standard curve of dilutions that corrects FACS percent positive to true percent positive.

3) Our very high label density with very low nonspecific binding (background) greatly minimizes the need for background correction. However, the greater precision required for accurate red cell volume and red cell survival measurements requires techniques for accurately estimating the background correction. We have developed and incorporated those techniques into this method as described below.

Concentrations of biotinylating agent (0.0002 to 2 mg/mL of RBC) and a range of incubation times have been explored to establish optimal biotinylation densities for different species, different applications (RCV versus RCS), sequential applications, and various detection systems. Linearity of dilution by unlabeled cells has been determined because proportional dilution is a fundamental principle of the in vivo method.

After washing and biotinylation, the labeled erythrocytes are incubated with a range of $^{125}$I-streptavidin concentrations to determine saturating conditions. Incubation time was varied (e.g., 1 hour, 4 hours, and 24 hours) to ascertain the time necessary to reach equilibrium (maximum counts bound).

A discrete separation of free $^{125}$I-streptavidin from $^{125}$I-streptavidin that is bound to the biotin moiety on the labeled red cell is required. We evaluated several washing methods as judged by the following criteria: 1) minimum non-specific binding of $^{125}$I-streptavidin to red cells that have not been biotinylated; 2) maximum binding of $^{125}$I-streptavidin; and 3) maximum binding that is stable when washed. As the method was scaled up for repetitive measurements, we explored other methods of cell washing that might be more effective or less time consuming or both. These methods were evaluated for their performance relative to the more labor intensive suspension/sedimentation procedure. For example, we used a dextran/metrizoic acid density separation that gave satisfactory results. In this method, the plasma, white cells, and platelets generally remain on the top or the intermediate part of the dextran gradient; red cells agglutinate and pellet at the bottom. Whether this density method permits excessive solvent trapping of the free $^{125}$I-streptavidin or non-specific binding of $^{125}$I-streptavidin will have to be determined empirically, but the density method has worked well in the experiments presented below. Use of silicon oil gradient or a non-protein binding membrane (e.g. 0.2µ nylon filters from Schleicher & Schuell, Inc., Keene, N.H.) may be acceptable alternatives to the preferred methods presented herein.

Although the biotin-binding characteristics of avidin and streptavidin are quite similar, some characteristics of the proteins as macromolecules are quite different. For example, the isoelectric point for avidin is pH=10, while that for streptavidin is pH=5. Thus, there may be some practical advantage of one protein over the other with respect to nonspecific binding to the surface of the erythrocyte. In the process of developing our current $^{125}$I-avidin assay for biotin, we have explored the use of $^{125}$I-streptavidin. Several observations from those studies may be relevant to the use of one protein over the other.

1. We have developed a simple and efficient method for purifying streptavidin from the supernatant of the culture of the yeast *Streptomyces avidinii*. As a result of these studies, streptavidin can be efficiently purified.

2. Streptavidin can be iodinated by the same method used to iodinate avidin.

3. $^{125}$I-streptavidin is as good as (but not better than) $^{125}$I-avidin in binding to biotinylated bovine serum albumin (BSA) that has been adsorbed to a solid phase.

4. Both $^{125}$I-avidin and $^{125}$I-streptavidin bind quite well to several biotinylated proteins (e.g. BSA and keyhole limpet hemocyanin (KLH)) whether biotinylated using NHS-LC-biotin or NHS-biotin; non-specific binding is low.

5. Detectable biotin concentrations in complex biologic fluids such as plasma are the same whether $^{125}$I-avidin or $^{125}$I-streptavidin is used in the assay.

Any biotin binding protein including, but not limited to, streptavidin and avidin may be used in the method of the present invention. It is not intended to limit the present invention to either avidin or streptavidin as set forth in the preferred embodiments.

EXAMPLE I

Sensitivity of the Non-radioactive Method

Figure 1:
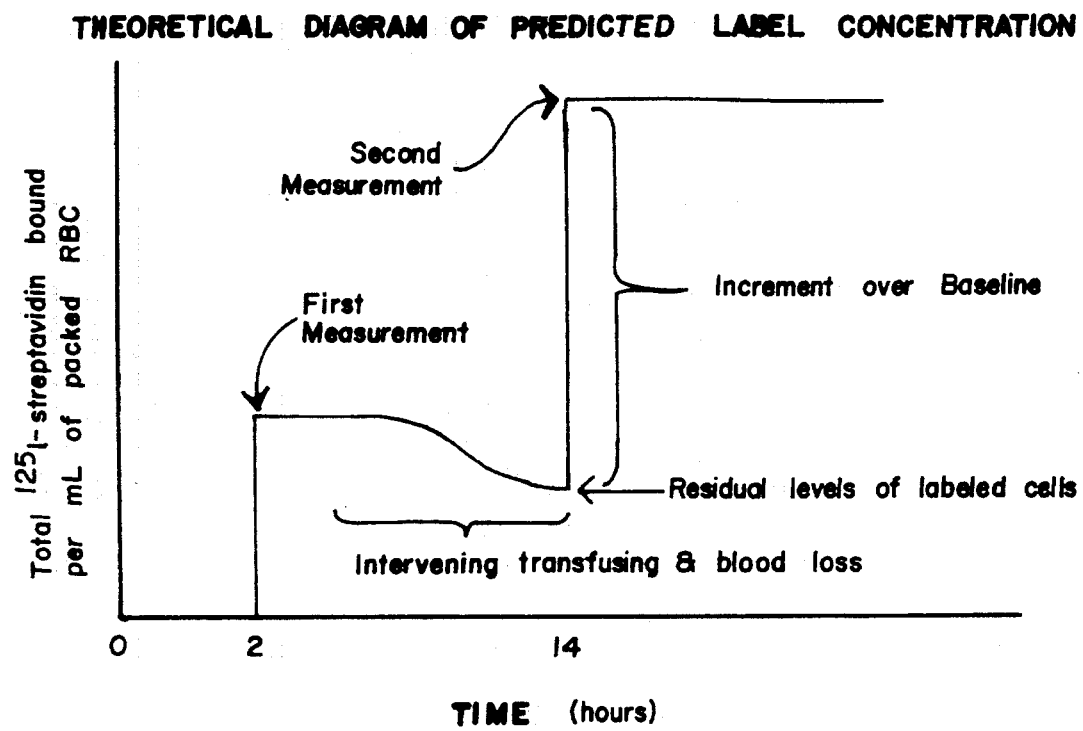
FIG. 1 is a diagram of predicted label concentrations

Repetitive measurements of red cell volume require successive increases in the total numbers of labeled cells (or the densities of the label on the cells) that are transfused with each measurement. One must also measure the residual amount of labeled cells remaining in circulation from the previous measurement of circulating red cell volume. FIG. 1 depicts the predicted time course of the concentration of labeled cells (as $^{125}$I-Streptavidin bound per mL of packed red blood cells (RBC's)) with two measurements of red cell volume.

The equation for calculating the first red cell volume is entirely analogous to that used for $^{51}$Cr.

$$RCV = I/C = S*D*V_i/C = S*D*V_i*B/H_v$$

Where

I=the total amount of injected label (e.g., $^{51}$Cr, $^{14}$C-cyanate or $^{125}$I-streptavidin binding capacity) in counts per minute C=the concentration of label in the red cells of the sample drawn after mixing is completed (cpm's per mL of red cells)

S=concentration of label in the diluted standard (cpm per mL)

D=the dilution factor for the diluted standard $V_i$=the volume of labeled red cell suspension injected (mL)

$H_v$=the packed cell volume of the whole blood sample corrected for plasma

B=the concentration of label in the blood sample drawn after mixing is completed (cpm per mL blood)

The equation for calculating each successive red cell volume is shown below and is analogous to that used for the hemoglobin F method.

$$RCV = C_a*V_i/(C_{k+1}-C_k)$$

Examination of this equation and FIG. 1 provides evidence that use of the same volume of cells for the second infusion (e.g., second infusion volume=100% of first volume used), would produce an increment in the total circulating labeled cells that is acceptable for the second measurement (~100%). However, by the seventh measurement the increment produced would be trivial (⅙=18%) because of accumulating "baseline" due to residual cells. Use of a small increment in the total concentration of label will greatly increase the total error because the relative experimental error inherent in measuring the increment is amplified if baseline ("background") is large compared to the increment ("signal"). Indeed, most treatments of incremental error indicate that the increment in the signal (e.g., in this case the concentration of label in the blood="the signal") must be at least equal to the baseline (i.e., the residual concentration of labeled cells in the blood) to minimize error. Thus, the amount of signal added must roughly double with each successive measurement. Similar approaches have been recommended to measure RCV using fresh red blood cells labeled with $^{51}$Cr and the PTR (post transfusion recovery) of stored red blood cells using $^{51}$Cr again. If we repeat measurements every 12 hours for 72 hours, the signal must double 6 times; hence the required range of operating accuracy for the method must be $2^6=64$. Hence we need a "linear dynamic range" of approximately 64 fold.

The following calculations support such a linear dynamic range with adequate sensitivity. For this discussion, sensitivity is defined as the ability to quantitate the biotin label on the red cell with acceptable accuracy (e.g. ±5% coefficient of variation).

First, to estimate sensitivity based on biotinylation density on the red cell surface, let us choose $2 \times 10^{10}$ labeled cells to assay for biotin label in each experiment; this is roughly the number of cells in 5 mL of blood with a hematocrit of 40. The biotinylation density reported by Cavill et al. is 3.6 μmol of label per mL of packed red blood cells (=1.42 μmol label/mL blood if hematocrit=40%). The stoichiometric bonding ratio of biotin to avidin is 4:1 and is used in this calculation as a worst case; in this application, steric factors on the red cells would probably limit the stoichiometry to 1:1 and increase the sensitivity. The specific radioactivity of 125I-avidin is $1.8 \times 10^3$ cpm per fmol of avidin (a typical value for $^{125}$I-avidin synthesized in our laboratory). Using these parameters, one can calculate the radioactivity that would be bound to the red cells in 5 mL of biotinylated blood:

$$\frac{\text{Radioactivity}}{\text{5 mL blood}} = 5 \text{ mL} \times \frac{1.4 \text{ μmol}}{\text{mL blood}} \times$$

$$\frac{1 \text{ μmol streptavidin}}{4 \text{ μmol}} \times \frac{1.8 \times 10^{12} \text{ cpm}}{\text{μmol }^{125}\text{I-streptavidin}} =$$

$$3.2 \times 10^{12} \text{ cpm/5 mL labeled blood}$$

If we choose 1.0 minute counting time and a minimum radioactivity of $10^4$ cpm per 5 mL sample to achieve counting statistics of ±1%, we have an excess of sensitivity of more than $10^8$. Of course, a portion of this excess sensitivity may be necessary to overcome practical experimental limitations. For example, on the seventh measurement, we do not want to give an amount of blood that importantly changes the blood volume or requires a substantial period of time to be delivered. Limiting the seventh infusion to 25 mL of the labeled blood, the first measurement of blood volume can use an infusion volume of cells of no more than 25 mL/$2^7$=0.2 mL. This 200 μL volume is feasible for handling and measuring accurately, particularly if diluted in a carrier fluid (e.g., the patient's own unlabeled blood or normal saline) to minimize "dead volume" losses.

With this limited volume in the first infusion, we obtain a practical amount of radioactivity for detection by the $^{125}$I detection system, despite dilution of this small sample in the large total blood volume of a normal adult. Let us assume the blood volume of a 70 kg patient is approximately 5,000 mL.

$$\frac{\text{Radioactivity}}{\text{5 mL blood sample}} =$$

$$\frac{\frac{3.2 \times 10^{12} \text{ cpm}}{\text{5 mL labeled blood}} \times 0.2 \text{ mL labeled blood infusion}}{5000 \text{ mL total blood volume}} \times$$

$$5 \text{ mL blood} = 6.4 \times 10^6 \text{ cpm/5 mL blood sample}$$

The sensitivity of the proposed method can also be calculated in relation to current operating limits of the $^{125}$I-avidin assay, which is used for determination of biotin in plasma, urine, cerebrospinal fluid, and milk. The assay consistently measures as little as 10 fmol of biotin per assay with a sample volume of 100 μl (i.e. 100 fmol/mL). Assuming the red cell biotinylation density of Cavill (0.36 fmol per cell), one can calculate the concentration of biotin residues (per mL labeled blood) as follows:

$$\frac{\text{biotin moieties}}{\text{ml blood}} = \frac{2 \times 10^{10} \text{ cells}}{\text{5 mL blood}} \times \frac{0.36 \text{ fmol biotin}}{\text{cell}} =$$

$$\frac{1.4 \times 10^9 \text{ fmol biotin}}{\text{mL labeled blood}}$$

Even with a 1/25,000 dilution of the labeled cells for the first volume measurement, the concentration of label will be approximately $5.6 \times 10^4$ fmol biotin per mL blood or $2.8 \times 10^5$ fmol biotin per 5 mL blood sample. This is more than 100 fold greater than the lower limit of the $^{125}$I-avidin assay ($10^2$ fmol/mL). These calculations suggest that we easily achieve a density of biotinylation high enough to give a wide assay range with adequate sensitivity.

EXAMPLE II

Stability of the Biotin Label

Figure 2:
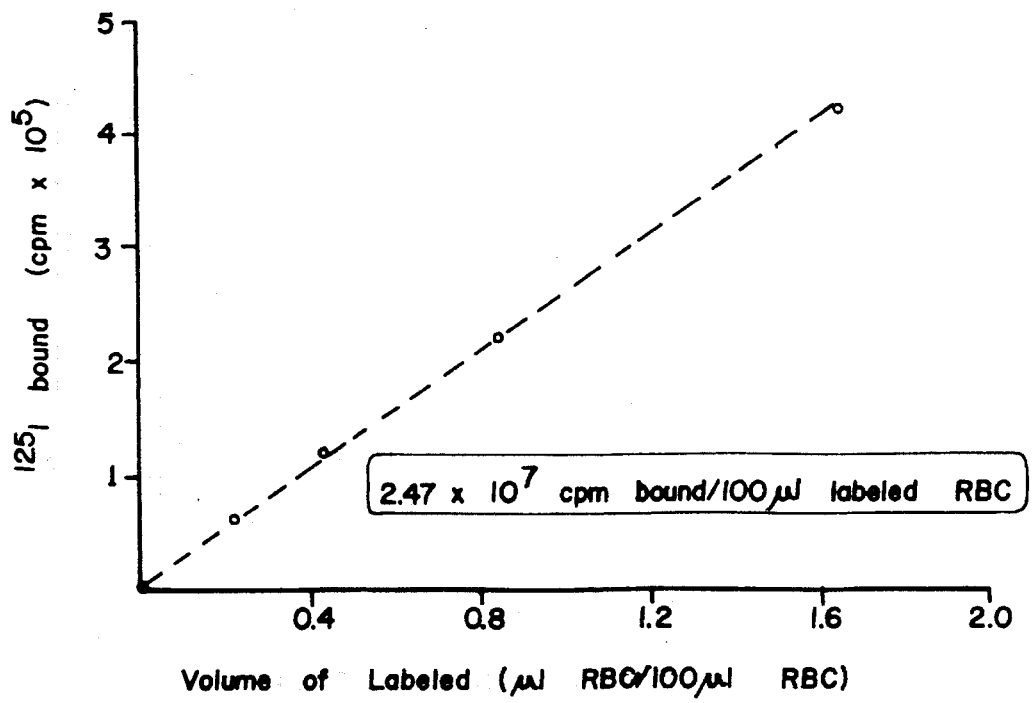
FIG. 2 is a graph showing biotinylation of human red blood cells.
Figure 3:
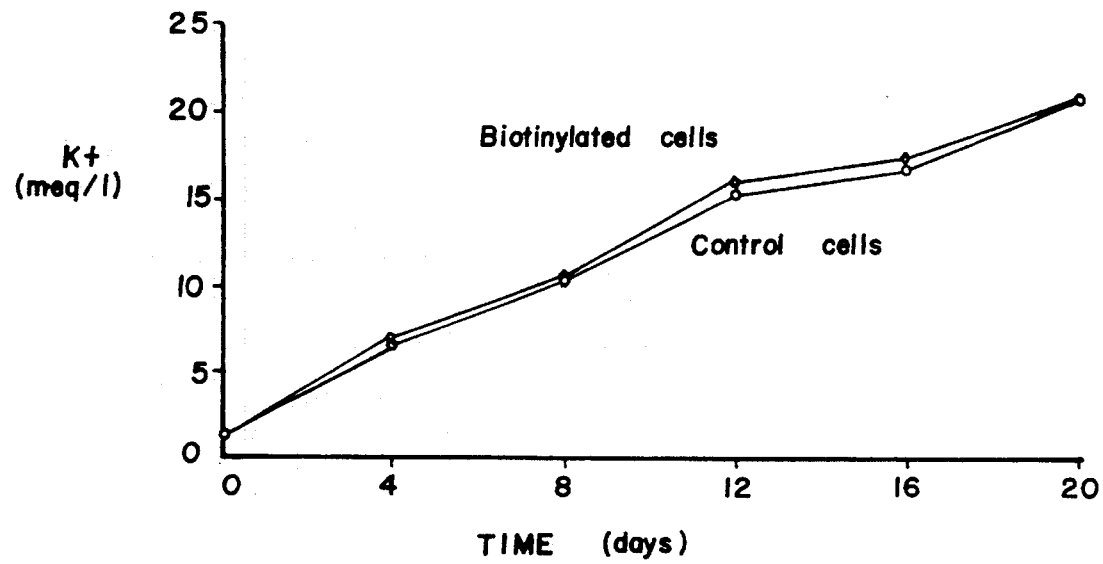
FIG. 3 is a graph showing release of potassium in vitro.
Figure 4:
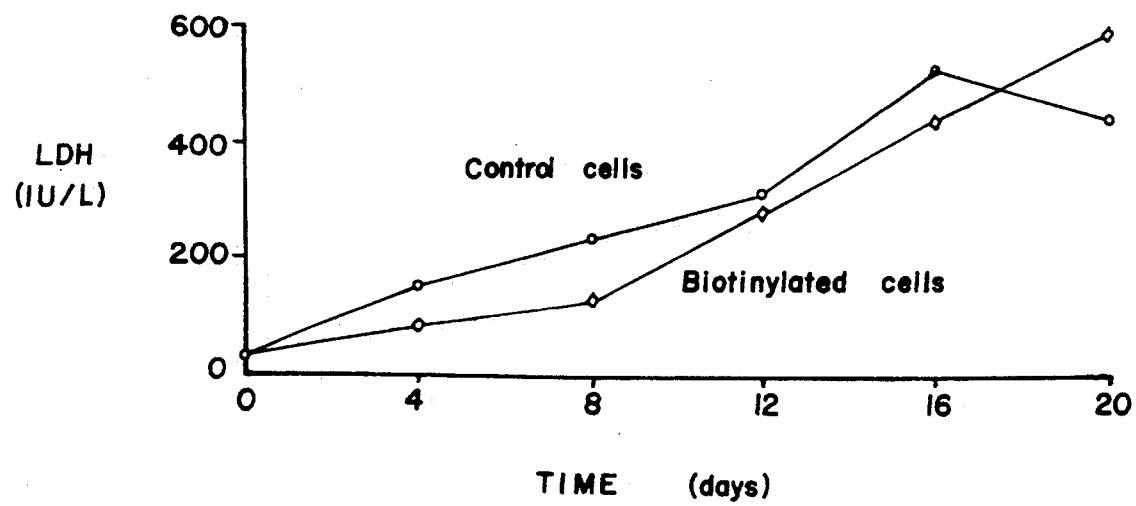
FIG. 4 is a graph showing release of LDH in vitro.
Figure 5:
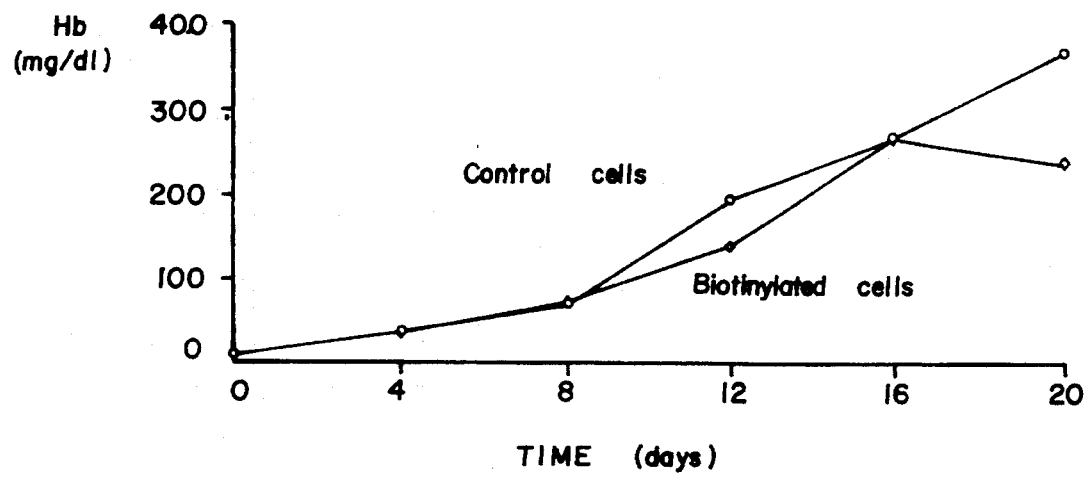
FIG. 5 is a graph showing release of hemoglobin is vitro.

As discussed below, one embodiment of the present invention includes a red cell washing method that removes loosely bound proteins and allows biotinylation only of firmly anchored proteins. As demonstrated by the in vitro experiments below, this produces a biotin label that is stable for several weeks. Concurrently with development of a stable label for human red cells, we have developed a suitable method for detection of the labeled cells. The labeled cells are incubated with $^{125}$I-streptavidin; then, free $^{125}$I-streptavidin is separated from that bound to red cells by dextran-metrizoic acid gradient centrifugation. Shown in FIG. 2 are data from one experiment developing the labeling method, testing the gradient separation of bound vs free $^{125}$I-streptavidin, and examining the linearity of dilution of labeled cells in unlabeled human cells from the same individual.

In this experiment, the cells were biotinylated at a density=1/100th that of a Cavill et al. in order to reduce the rate of consumption of $^{125}$I-streptavidin. Despite this reduction, 0.2 mL of these cells could be infused into a 70 kg patient (producing a 1:25,000 dilution), and the resulting label density in vivo would be $5 \times 10^4$ cpm/5 mL blood.

In vitro studies of injury and stability of labeled human red blood cells have examined whether the label is stable chemically and whether biotinylatin damages the cells leading to rapid removal of the cells from circulation. In the context of red cell volume measurements, "rapid removal" should be defined as significant loss before mixing is complete and the in vivo blood sampled can be obtained (about 5 minutes).

In the method of the present invention, the cells are not damaged and the label is stable (in vitro) for days. As depicted in FIGS. 3, 4, 5, and 6, we examined whether labeling with biotin would injure the cells, leading to leakage of intracellular components. Aliquots of human red blood cells were washed, labeled with biotin ("biotinylated cells") and then suspended in Adsol® (a standard red cell storage medium containing a saline, adenine, glucose, and mannitol; Fenwal Laboratories, Round Lake, Ill.). Control cells were washed and stored in Adsol®; these cells were not biotinylated. At four day intervals, we measured the concentrations of K+ (the anion with the highest intracellular concentration), lactate dehydrogenase (LDH, a common marker of red cell hemolysis), and hemoglobin in the storage medium containing either biotinylated cells or control cells. FIGS. 3, 4, 5 and 6 depict single values reported by the clinical laboratory.

The increases in the concentrations of K+, LDH, and hemoglobin are similar for biotinylated and control cells for storage up to 12 days. Thus, biotinylation at this level does not damage the cells as judged by these criteria. More precisely stated, the experiment provides evidence that the damage of biotinylation per se appears to be negligible compared to the damage of handling and storage. In this preliminary storage study, we did not evaluate cells that had been neither washed nor biotinylated (to assess the effect of washing per se). However, one can compare the leakage of K+ from our cells to that of red cells stored in Adsol® as reported by A. Heaton, et al., "Use of Adsol preservation solution for prolonged storage of low viscosity AS-1 red blood cells," British Journal of Haematology, 1984. After 35 days the concentration seen by Heaton (46.1±2.3 meq/l) is similar to those depicted in FIG. 3; this similarity indirectly suggests that the washing process did not injure the cells.

Figure 6:
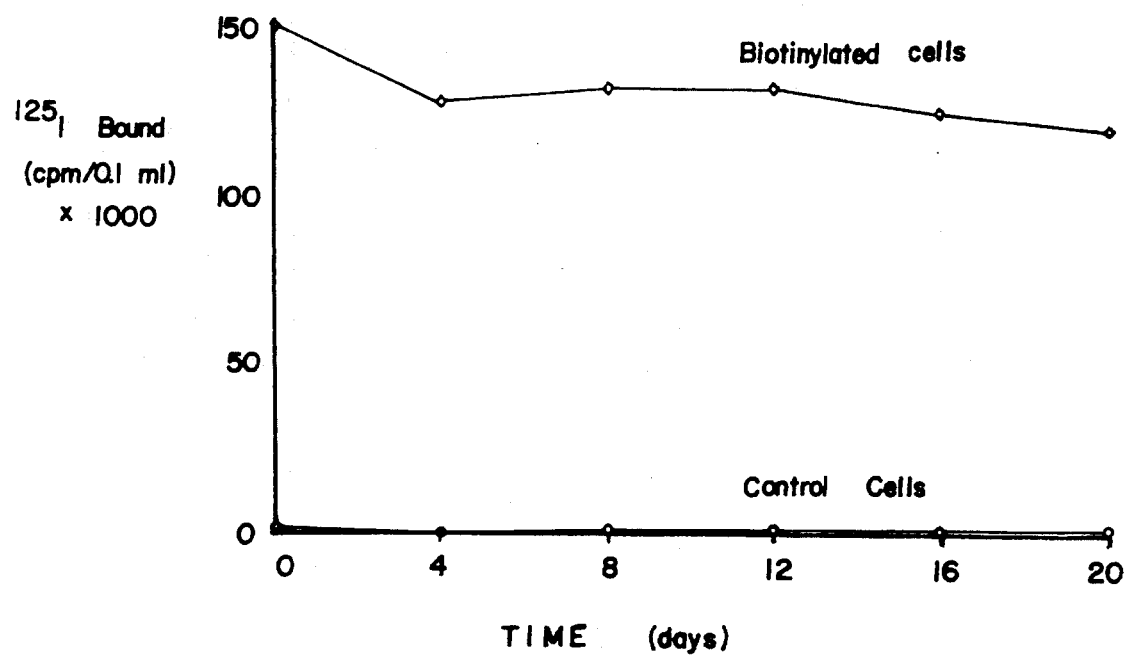
FIG. 6 is a graph showing stability of the label in vitro.

We also examined whether the label would elute from the cell surface (e.g., by diffusion or cleavage). In the same experiment, we measured the concentration of label as $^{125}$I-streptavidin binding capacity. These data provide evidence that the biotin label is stable in Adsol® for at least 12 days (FIG. 6).

EXAMPLE III

Feasibility of a Biotin Label

We have proceeded with investigation of biotin and $^{14}$C-cyanate labeling of sheep red blood cells and with demonstration of our ability to label sheep red blood cells with $^{51}$Cr using the standard method.

Figure 7:
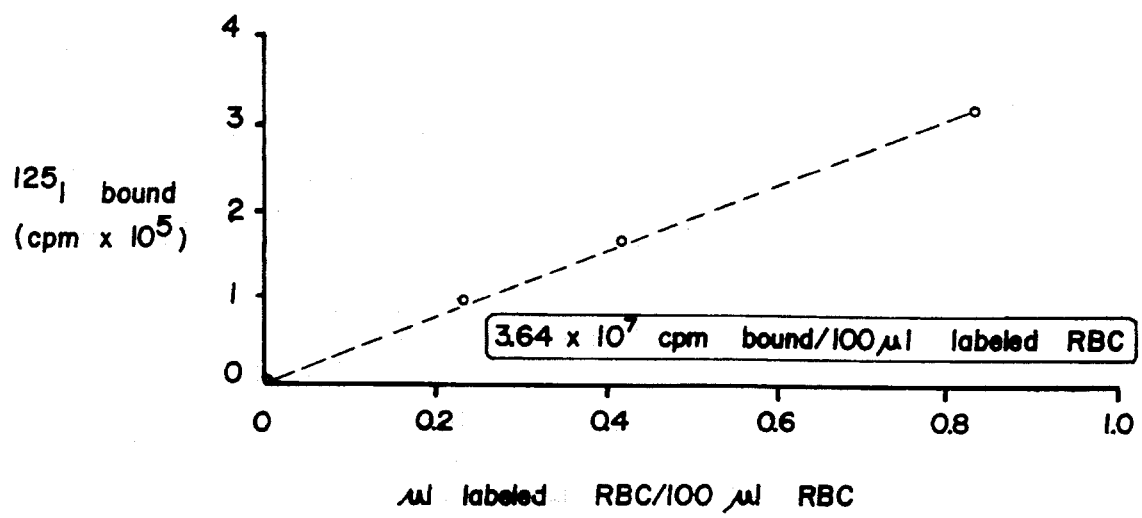
FIG. 7 is a graph showing biotinylation of sheep red blood cells.
Figure 8:
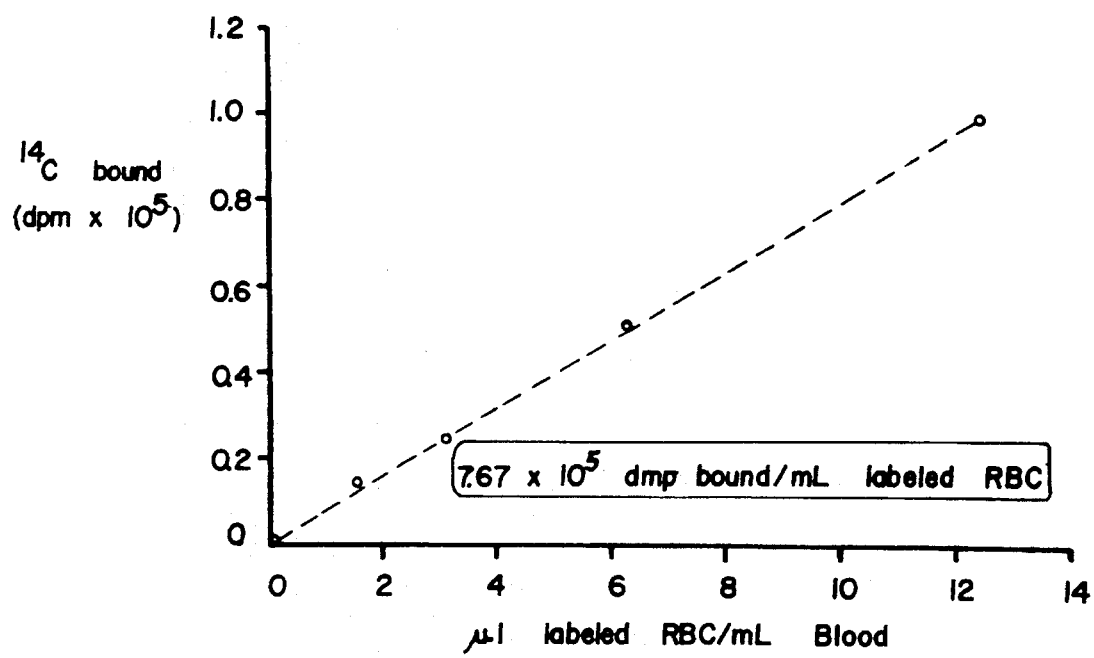
FIG. 8 is a graph showing $^{14}$C labeling of sheep red blood cells.

As shown in FIG. 7, we are able to label sheep cells at a high biotinylation density. Indeed, we used the same 100 fold reduction of biotinylation density to minimize consumption of our $^{125}$I-streptavidin. Dilution of the labeled cells in unlabeled autologous sheep cells was linear (FIG. 8). In addition, we demonstrated stability of the biotin label for several days.

Figure 9:
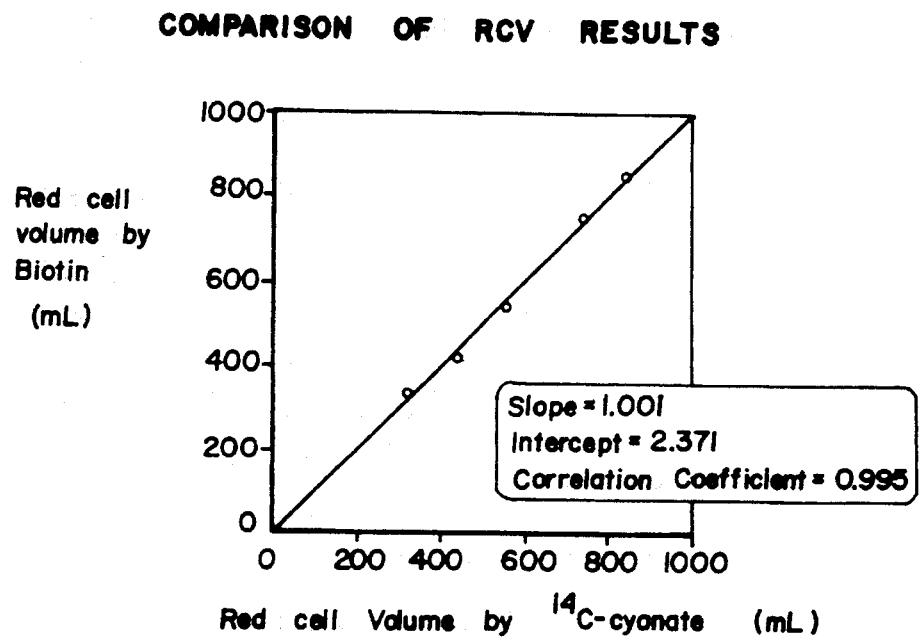
FIG. 9 is a graph comparing red cell volume results.

As shown in FIG. 9, we were able to label sheep cells with $^{14}$C-cyanate and to demonstrate linear dilution of labeled cells in unlabeled cells. The $^{14}$C-cyanate label was also stable during in vitro storage. Sheep cells were also labeled with $^{51}$Cr using standard methods; dilutions of $^{51}$Cr labeled cells in unlabeled cells were also linear.

FIGS. 7 and 8 compare red cell volumes determined by $^{14}$C-cyanate to those determined by the non-radioactive biotin method. The relationship between the volumes by the two methods is quite linear. The slope of the regression line is very close to 1 and the intercept is near 0. These data provide convincing evidence that this non-radioactive method does accurately measure red cell mass.

Our preliminary $^{51}$Cr volumes were consistently less than the volumes for the biotin and $^{14}$C-cyanate methods. Using more careful gravimetric techniques and by carefully removing any free $^{51}$Cr from both infusate and the blood sample obtained in vivo, we have conducted two blood volume determinations in which the $^{51}$Cr and $^{14}$C-cyanate values agreed quite well as shown in the Table 1.

TABLE 1

| | In Vivo Determination of RBC Volume in Two Sheep | | | |
|---|---|---|---|---|
| | SHEEP #1 | | SHEEP #2 | |
| Method | RBC Volume* (mL/kg) | Blood Volume* (mL/kg) | RBC Volume* (mL/kg) | Blood Volume* (mL/kg) |
| $^{51}$Cr | 21.4 ± 0.2 | 70.2 ± 0.6 | 21.7 ± 0.1 | 73.2 ± 0.4 |
| $^{14}$C-cyanate | 20.7 ± 0.5 | 68.0 ± 1.7 | 21.2 ± 0.4 | 71.5 ± 1.4 |
| Published $^{51}$Cr** | 21.1 ± 2.2 | 74 ± 5 | | |

*Mean ± 1SD of triplicate points extrapolated to zero.
**From Wade and Sasser Body water, plasma volume, and erythrocyte volume in sheep, American Journal of Veterinary Research (1970), p. 1375-8; n = 40 using $^{51}$Cr For the experiment presented in Table 1 and FIG. 9, autologous red cells were individually labeled with either biotin, $^{14}$C-cyanate, or $^{51}$Cr. The values for total red cell volume and total blood volume were calculated from labeled RBC concentrations at time=0; these were obtained by linear extrapolation to time=0 of the blood concentrations of each label (3 or 4 points spaced from 5 to 30 min). Linear extrapolation was used rather than first order exponential extrapolation because the data fit best to a linear plot and because first order extrapolation did not produce importantly different results. The standard deviation values shown in the table were obtained from the coefficients of variation of triplicate blood sampling in each time point. The standard deviations of the extrapolated values using the linear regression are generally even smaller than the standard deviations of the triplicate points. The average range for the 95% confidence limit was only 1 mL/kg for the three RCV estimates and was 3.6 mL/kg from the three blood volume estimates.

EXAMPLE IV

Validation of the Reference $^{14}$C-cyanate Method for RCV and RCS.

Figure 10:
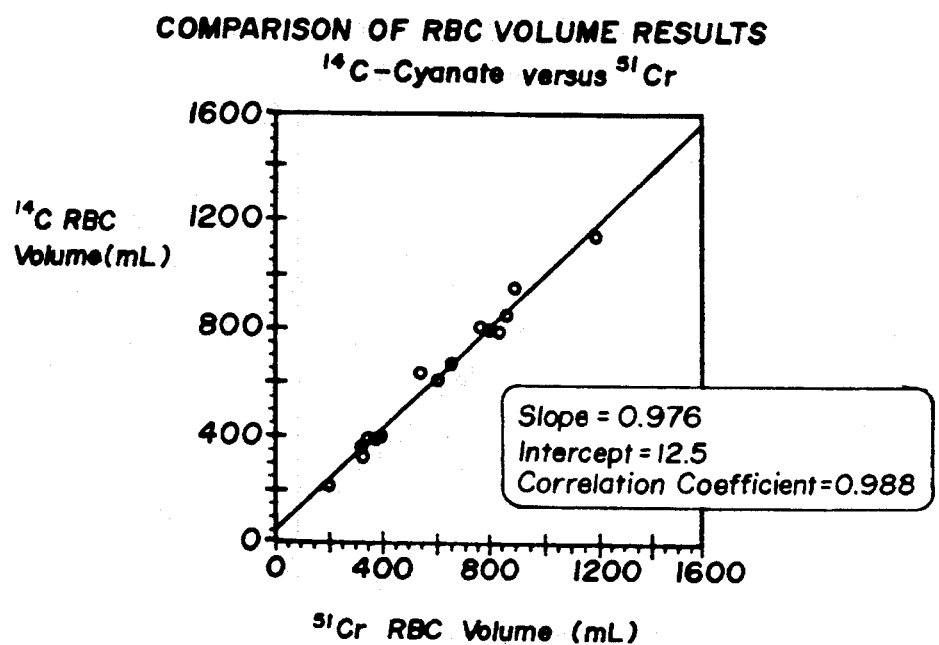
FIG. 10 is a graph comparing red cell volume results: $^{14}$C-Cyanate versus $^{51}$Cr.

RCV by $^{14}$C-cyanate:

$^{51}$Cr is the industry accepted "gold standard" for measuring red cell volume and red cell survival in human subjects. Because $^{51}$Cr is not a suitable method of measuring red cell survival in sheep, we developed a method for $^{14}$C-cyanate labeling of red cells that agrees very well with $^{51}$Cr measurements of red cell volume as shown in FIG. 10.

Figure 11:
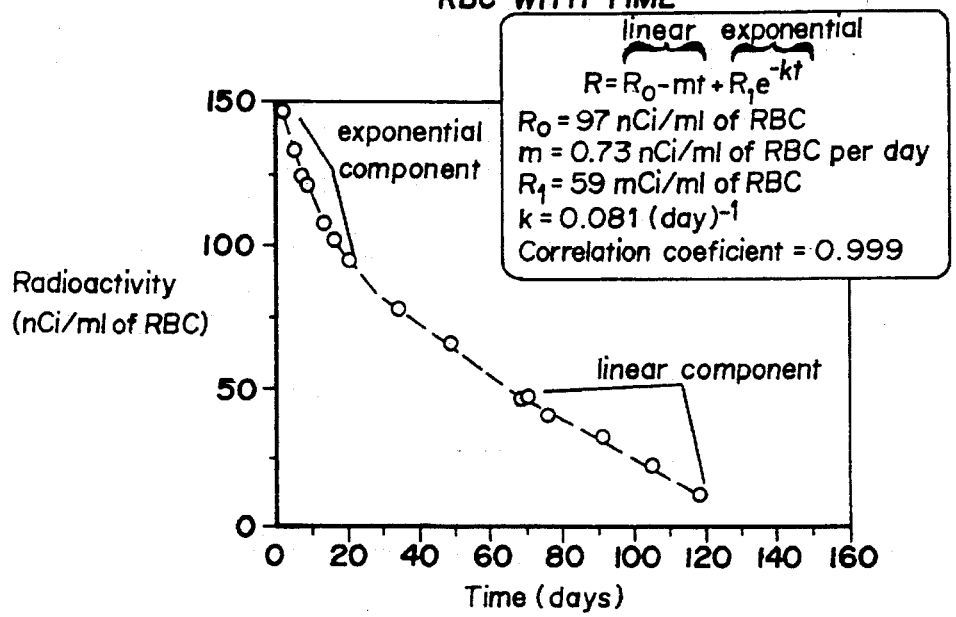
FIG. 11 is a graph showing decline in $^{14}$C-Cyanate labeled red blood cells with time.
Figure 12:
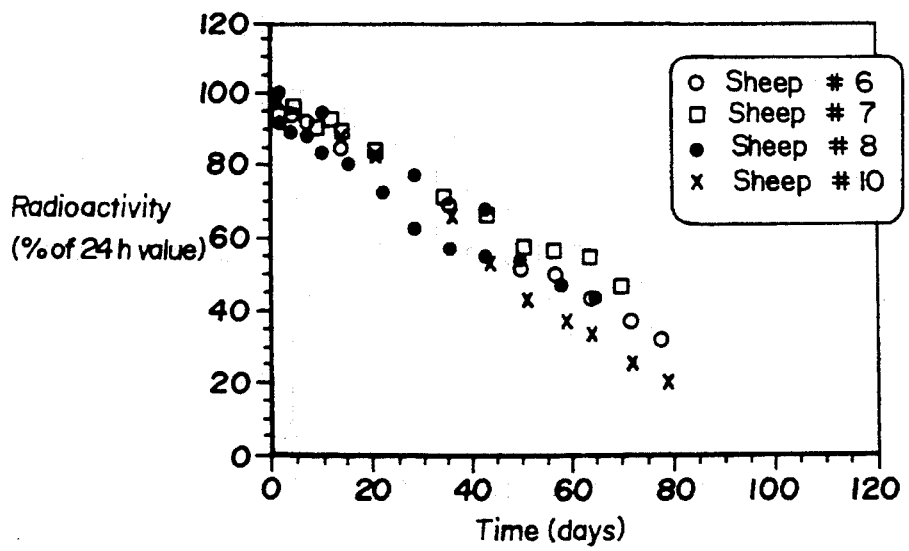
FIG. 12 is a graph showing survival of $^{14}$C-Cyanate label.

RCS by $^{14}$C-cyanate:

Initially, we developed an efficient method of permanently labeling sheep RBC with $^{14}$C-cyanate and studied RBC kinetics in 5 sheep. As shown in FIGS. 11 and 12, RBC survival after day 1 ($^{14}$C per mL RBC vs time) accurately fit a model containing two components:

(a) an early exponential loss of cells reflecting damage caused by labeling; and (b) a later, linear phase reflecting survival of undamaged RBC in vivo.

In the first 5 sheep, an excessive proportion of RBC (40–60%) exhibited exponential disappearance, preventing determination of true mean potential life span (MPL) until more than 3 weeks after initial infusion of labeled RBC.

TABLE 2

Parameters of Survival for $^{14}$C-Cyanate Label

| Sheep # | Observation (days) | Remaining by 24 hr (%) | % linear | MPL | half-life of exponential |
|---|---|---|---|---|---|
| 2 | 118 | 83% | 66% | 133 | 8.5 |
| 3* | 21 | 88% | 65% | 143 | 6.0 |
|  | 63 | 87% | 76% | 180 | 17 |
| 4 |  |  |  |  |  |
| 5 | 77 | 79% | 42% | 124 | 18 |
| 6 | 71 | 72% | 100% | 110 | NA |
| 7 | 69 | 83% | 100% | 132 | NA |
| 8 | 72 | 86% | 100% | 113 | NA |
| 9 | 58 | 77% | 85% | 78 | 15 |
| 10 | 78 | 82% | 100% | 96 | NA |
| 12* | 36 | 79% | 100% | 112 | NA |

*Referenced to Day 2

In 1993, we developed less harsh conditions for $^{14}$C-cyanate labeling and were able to consistently limit the exponential population to <5% of total RBC labeled (Sheep 6–12 on Table 2. above). The range of MPL obtained from the linear phase agreed well with those published by E. M. Tucker, "Red cell life span in young and adult sheep," Res. Vet. Sci., 1963, using radioactive $^{59}$Fe pulse/chase in sheep. These studies provide strong evidence that survival of sheep RBC after 24 h can be accurately assessed with $^{14}$C-cyanate labeled RBC.

EXAMPLE V

RCV by Biotin Method

Figure 13:
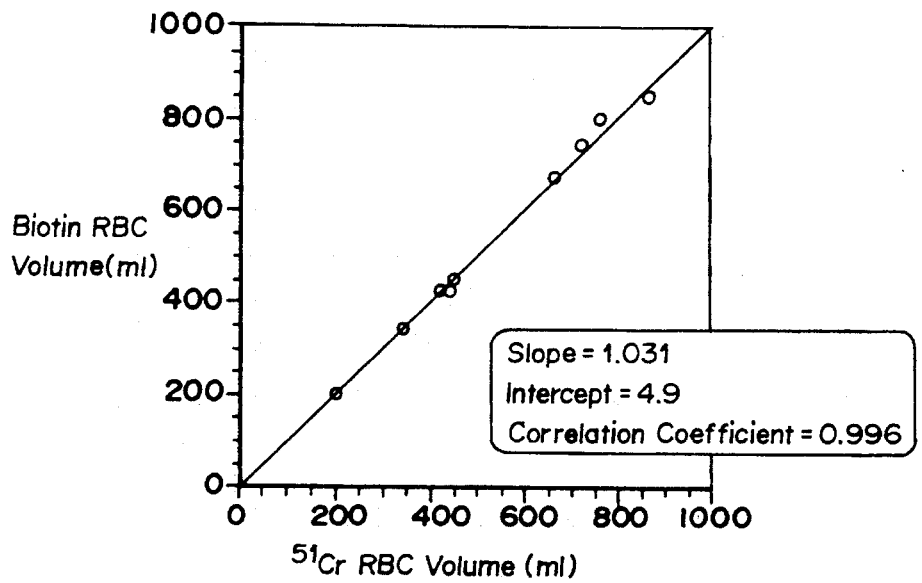
FIG. 13 is a graph comparing red blood cell volume results: biotin versus $^{51}$Cr.
Figure 14:
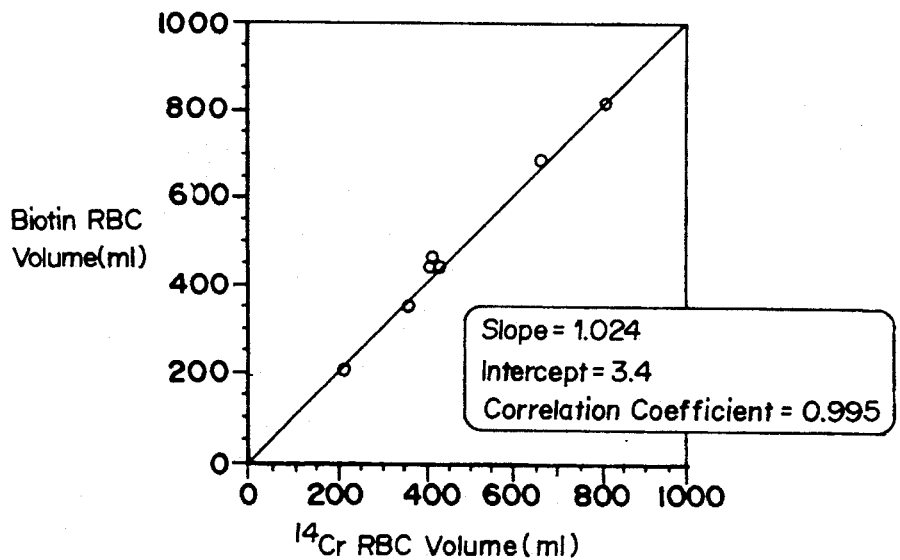
FIG. 14 is a graph comparing red blood cell volume results: biotin versus $^{14}$C-Cyanate.

We can accurately measure the RCV in the sheep over a range of body weights using either the biotin $^{125}$I-avidin method or the biotin FACS method (discussed below). For RCV, both the standard $^{51}$Cr method and the newer $^{14}$C-cyanate method can serve as references, as shown in FIGS. 13 and 14.

EXAMPLE VI

Limitations and Further Validation of the Biotin $^{125}$I-streptavidin and Biotin FACS Methods In studies to establish the practical limits of the biotin methods for RCV, we studied sheep as young as the immediate post-weaning age (7 wk; approximately 10 kg). We have established that accurate measurements can be made in vivo using as little as 500 μl of blood withdrawn at 5 minutes and assayed in duplicate after the infusion of a volume of biotin labeled RBC equal to about 1% of the animal's circulating RCV. We define acceptable accuracy as coefficient of variation of ±5% around the true RCV as measured by $^{51}$Cr or $^{14}$C-cyanate. Triplicate assays require ~700 μl of blood per time point; extrapolation to zero requires 3–5 time points. To further explore measurement capabilities in blood volume similar to those of low birth weight infants, in vitro experiments were conducted using the model of human circulation described below. Circulatory blood volumes as small as 40 mL and infusion of as little as 1 ml of labeled cells were studied. Sampling of 700 μl blood allowed precision of ±3% (e.g., a coefficient of variation of among triplicate assays) and accuracy of ±5% versus the RCV (or blood volume) determined gravimetrically, by 51Cr, or by 14C-cyanate.

To determine whether the biotin label is stable at 4° after being in circulation, this in vitro study investigated the situation under which samples in the human validation study could be batched and sent to us on ice for analysis in our laboratory. This study also explored label stability when the biotin labeling was done using two different methods: the "wash" method and the "lysine" method discussed below in Examples VIIa and VIIb, respectively.

TABLE 3

Effects of temperature and time on biotin label loss

| Human Cells Label Method | Day | Stored 4° C. | Stored 37° C. | Stored 37° C. then 4° C. Blood @ 37° C. | Stored 37° C. then 4° C. Blood @ 4° C. |
|---|---|---|---|---|---|
| Lysine | 0 | 100.00% | 100.0% | 100.0% |  |
|  | 1 | 105.8% | 92.5% | 92.5% | 100.0% |
|  | 2 | 94.0% | 60.8% | 78.8% | 85.1% |
| Wash | 0 | 100.0% | 100.0% | 100.0% |  |
|  | 1 | 98.8% | 91.4% | 91.4% | 100.0% |
|  | 2 | 99.6% | 82.6% | 87.3 % | 95.5% |

EXAMPLE VIIa

Cell Washing Method

Our studies suggest that thorough washing of the red cells prior to biotinylation is critical for stable labeling. Cells are collected in AS-1 system of blood storage (Fenwal Laboratories); the initial anticoagulant is citrate-dextrose-phosphate (CDP), and the red cell storage medium is Adsol®. For cell washing, 2.5 mL of packed cells are suspended in 10 mL of 20 mM sodium phosphate, 0.155M NaCl, pH=7.4 with 22 mM glucose. Cells are then sedimented at 1500 xg for 10 min. The supernatant is discarded. This washing step is repeated four times. A phosphate buffered saline (PBS) solution with glucose was chosen for washing because it contains approximately the same final concentration of glucose as the CDP into which blood is routinely collected and as the Adsol R in which the washed red cells will be stored.

EXAMPLE VIIb

Lysine Labeling Method

In subsequent experiments, biotin labeling was done by one of two methods. The first method is the standard wash method. The method is very labor intensive and time consuming. The method produces a subpopulation of labels that are stable; however, the labeling process stresses the RBC enough that our 24 hour post-transfusion recoveries (PTR24) appear to be low (less than 80%). However, true 24 hour post-transfusion recoveries (PTR24) in vivo are uncertain at this point because two competing processes are happening simultaneously:

1. removal of RBC from circulation; and
2. loss of label from the RBC surface.

We had hoped to use the $^{14}C$-cyanate as the marker for true post-transfusion recovery of RBC that were doubly labeled with $^{14}C$ and biotin. However, as detailed above, it is likely that free $^{14}C$-cyanate within RBC continues to bind during the first 24 hours in vivo producing an artifactual overestimate of the true PTR24.

We have developed a second method for biotin labeling that addresses some of the disadvantage of the first method. The second method involves direct biotinylation of packed sheep RBC with no prior washing of the RBC. Lysine then is added to provide a substrate with which the biotinylation reagent will react, stopping the reaction. For the lysine method, the possible advantages potentially include time savings, and better PTR24, easier adaptation to sterile techniques.

Blood was collected in heparin. RBC were sedimented by centrifugation at 2000 rpm for 10 min. The plasma and buffy coat were removed by suction. Biotinylating reagent (either NHS-LC-Biotin or Sulfo-NHS-Biotn), in amounts varying from 0.2 to 2 mg/mL of packed RBC was added and incubated for 1 hour at room temperature. 1 mg of lysine/mL packed RBC was added and the mixture was incubated at 37° for 1 hour before infusion. 200 μl samples (both "infusate" and "model blood volume" samples) were washed three times with 3 mL of PBS-glucose before addition of 100 μL of $^{125}I$-streptavidin. This mixture was incubated and separated on the dextran-metrizoic acid gradient as before.

This experiment investigated the usefulness of the RBC labeled with biotin by the lysine method in an in vitro determination of RBC volume. Human RBC were used and a 50 mL model blood volume was chosen.

One milliliter of packed RBC were incubated with 2 mg of Sulfo-NHS-Biotin in 0.5 mL PBS+glucose for one hour at 37° C. After incubation, 10 mg of Lysine (20× molar excess) in 0.5 mL with PBS was added to the RBC and incubated for 1 hour at room temperature. Prior to the assay by the $^{125}I$-SA method, samples from the model blood volume were washed 3× with 3 mL of PBS+glucose to remove residual free biotinyl-lysine. As shown in the Table 4. below, the biotin volume agreed very well with the gravimetric volume suggesting that the lysine method will reduce labeling effort and time and result in RBC with an increased PTR24.

TABLE 4

| RCV In vitro by Lysine Method | | |
|---|---|---|
| Biotin Volume (ML) | Gravimetric Volume (mL) | Percent Difference |
| 36.46 | 36.54 | −0.22% |

EXAMPLE VIII

Sequential Volume Determinations

Some applications of the nonradioactive method for RBC volume require that two successive measurements be made in the same subject. We have chosen the phrase, "sequential volume determinations" to apply to this application of the nonradioactive method.

Because of problems with label persistence at 37° and in vivo, we elected to add in a more intensive exploration of fluorescence sorting as a method of determining survival of biotinylated RBC. Because label loss was apparently occurring by both an exchange mechanism and cleavage from the RBC surface, it was concluded that it was not likely we would be able to completely prevent these processes simply by changing the biotinylating agent or some other maneuver suitable for application of the method to low-birth weight infants. However, the observation that a portion of the label remained permanently attached to the RBC in vivo suggested that the careful washing and labeling techniques of our procedure was producing a subpopulation of labels on each RBC that do not leave the RBC and accurately reflect RBC persistence in circulation. On this basis, we examined the detection of biotin labeled RBC using fluorescein-conjugated avidin (FITC avidin), rather than $^{125}I$-streptavidin, with subsequent identification by fluorescent activated cell sorting (FACS). Because FACS is an enumeration method rather than a total label quantitation method, the possibility exists that we can measure the percent of RBC lost from the circulation over 24 hours (and perhaps over many days) despite the loss of more than half of the label from each RBC. We determined the utility of FACS for RCS and RCV measurements empirically in the sheep model and with human cells in vitro before attempting the more tedious and costly clinical studies. From this point forward, the two methods will be referred to as the "biotin method" and the "FACS method" although both use biotin.

To over simplify a complex problem, our application of FACS differed from other users of FACS. Other users seek to quantitate different RBC types that constitute a larger percentage of the population in question; for most FACS users the accuracy of the percentage is also less critical. For example, a common use of FACS would be to determine the number of CD3 positive lymphocytes as a percentage of the total lymphocyte count; whether the CD3 lymphocytes were 74.5% or 75.3% is not an important difference to most users of FACS. Moreover, most users of FACS would be quite content with the degree of linearity of dilution displayed in FIG. 15.

In contrast, measurement of RCV and RCS to ±5% accuracy requires very accurate determination of the dilution of the biotinylated RBC in unlabeled RBC. A typical percentage would be 1.05% of the total; we need to distinguish 1.05% from 1.09% of the total. Experience in particle physics suggests enumeration of events as a small percentage of a very large number of events is possible with the type of electronics and event accumulators used in FACS. What is needed is a reformulation of ideas on how to use the machine, especially in relation to event accumulation before buffer saturation. We reconfigured the counting approach (e.g., reset the windows) to collect adequate numbers of the small population of labeled RBC. We also examined several ranges of label density and incubation concentrations of FITC avidin and have produced a very discrete population of labeled RBC.

40 ml of human blood were used in our in vitro model of blood volume. A small amount of RBC were biotinylated with 0.4 mg of sulfo-NHS-biotin per mL packed cells using the lysine method.

As shown in the Table 5. below, the biotin volumes for the first two sequential determinations are sufficiently accurate for our purposes. We concluded that the biotin method with lysine label/wash method does work in vitro.

TABLE 5

| SVD 9 | Grav Vol (ml blood) | Biotin Vol (ml blood) | Biotin Vol % Dif. | FACS Vol (ml blood) | FACS Vol % Dif. |
|---|---|---|---|---|---|
| Vol. #1 | 40.4 | 39.0 | −3.5% | 38.6 | −4.5% |
| Vol. #2 | 39.1 | 37.4 | −4.3% | 36.6 | −6.5% |

The FACS results tabulated above include corrections. For both unlabeled red cells whose endogenous fluorescence places them in the detection grid for labeled cells and for the inherent non-linearity of the FACS device at low percent positives. On careful consideration, we reasoned that the FACS blood volume must be accurate if the volume ratios of the dilutions were truly accurate and if the FACS machine was accurately quantitating those dilutions because the FACS RCV method is based on the principal of linearity of dilutions of labeled RBC in unlabeled RBC. We sought to more carefully examine the relations between actual dilution and percentage of positives on the FACS machine, particularly at the low end of the range. Dilutions of the infusate were made from the 100% Positive infusate; these were assayed by FACS. As shown in the FIG. 15, the FACS % Positive was plotted against the Actual % Positive. Note that in the expanded lower end of the dilution curve, there is a consistent 18% error (i.e., the slope is 1.18 instead of 1.0, the line of identity). The source of the error is unknown; the possible sources include the following:

1. An inherent nonlinearity of the FACS enumeration process when events of interest are a small percentage of the total RBC being counted (a likely explanation).

2. Inaccurate volumes delivered by the pipettes used for the dilutions. This is a very unlikely explanation because the pipettes in our laboratory are gravimetrically calibrated to 0.5% accuracy and 0.5% precision approximately every 3 months. The pipettes used in these experiments were checked gravimetrically and met these specifications.

The line equation shown in FIG. 16 was used to correct FACS % Positive to Actual % Positive. The first two volume determinations by FACS approach an acceptable accuracy and agree.

This sequential volume experiment examined the effects of reduced biotin label density. Human RBC were labeled with 0.2 mg sulfo-NHS-biotin/mL packed RBC by the lysine method. Weights of infusate were 0.1063, 0.1057 and 0.2060 gm diluted into a 10 mL model blood volume for approximate dilutions of 1/400, 1/400, and 1/200. Correction of FACS % Positive to Actual % Positive was done in the manner described above. All three biotin volume estimates fell into the linear range of cmp/gm infustate dilutions.

As shown in Table 6. below, the volume estimates generated by both methods show better accuracy; only Biotin Volume #3 and FACS Volume #1 are outside the acceptable range.

TABLE 6

| SVD 10 | Grav Vol (ml blood) | Biotin Vol (ml blood) | Biotin Vol % Dif. | FACS Vol (ml blood) | FACS Vol % Dif. |
|---|---|---|---|---|---|
| Vol. #1 | 39.2 | 38.7 | −1.4% | 43.2 | 10.0% |
| Vol. #2 | 37.0 | 37.8 | 2.1% | 38.4 | 3.6% |
| Vol. #3 | 34.9 | 38.1 | 9.4% | 35.2 | 0.8% |

A series of experiments were done to establish the operating characteristics of the FACS machine for sheep red blood cells which are approximately half the size of human red blood cells and have red blood cell counts per millimeter of blood that are about twice as large as human cells. After the appropriate adjustments for these facts, we conducted a series of in vivo studies of both the biotin intragration and the biotin FACS methods as described above.

EXAMPLE IX

Additional Preliminary Studies of Biotin and FACS Methods in vivo

We sought to determine blood volume and RBC survival in vivo labeling. Both biotin quantitation and FACS were used for determination of RCV and RCS.

The animal used was a young male (weight=18.64 kg). RBC were labeled using $^{51}$Cr, $^{14}$C-cyanate, and sulfo-NHS-biotin. The biotin labeling was done by the lysine method with no prewashes and with a single postwash. Samples were washed 3 times to remove residual biotinyl-lysine before addition of $^{125}$I-SAv. FACS results were corrected by subtraction of % False Positives and by conversion of FACS % Positive to Actual % Positive. Because hematocrits and resultant RBC from Culter counting were suspect, RBC was calculated from hematocrits determined by the microcapillary tube method and MBC from Coulter counting.

TABLE 7

| Single in vivo RBC and Blood Volumes by Four Methods | | | | | | |
|---|---|---|---|---|---|---|
| | Biotin | 14C | 51Cr | FACS | MEAN | C.V. |
| RBC Vol (ML) | 361 | 370 | 355 | 356 | 361 | 1.9% |
| Blood Vol (mL) | 1181 | 1209 | 1161 | 1166 | 1179 | 1.8% |

After making two breakthroughs in the area of FACS, we have conducted additional in vivo sheep studies that provide solid evidence that red cell volume determined by the combination of the biotin label/FACS is as accurate as the original biotin method. The data are shown in FIGS. 16A, 16B and 16C.

In another experiment we attempted to measure RCV of a sheep sequentially using the 4 methods. Sulfo-NHS-biotin at a concentration of 0.05 mg/mL packed RBC was used to label the RBC. The wash method was used for labeling. Sample size was 100 ul with 100 μl of unlabeled blood to bring the total volume to 200 μl for assay. The $^{51}$Cr and $^{14}$C were assayed by the usual methods. The initial dilution for each label was 1:200 with a second 1:200 dilution for a total dilution in the animal of 1:100.

This sheep had been used in a previous study; residual biotin label RBC and residual 14C-cyanate labeled RBC were detectable in circulation; correction was made as usual.

TABLE 8

Sequential in vivo Blood Volumes by Four Methods

| Measurement | Biotin | 14C | 51Cr | FACS | MEAN | C.V. |
|---|---|---|---|---|---|---|
| 1 | 1705 | 1596 | 1667 | 1748 | 1679 | 3.9% |
| 2 | 1796 | 1637 | 1776 | 1869 | 1759 | 6.1% |

Although RCV by FACS tended to a higher value, the 4 methods agreed reasonably well. We have now successfully measured red cell volume and blood volume twice in one day in one sheep and daily for 3 days in one sheep using each of the 4 methods. Volumes agreed well between the methods as shown in Tables 9 and 10 below.

TABLE 9

In Vivo Sequential RCV on Same Day by Four Methods

| RCV (mL) | | | | % Difference vs $^{51}$Cr | | |
|---|---|---|---|---|---|---|
| $^{51}$Cr | $^{14}$C | Biotin | FACS | $^{14}$C | Biotin | FACS |
| 436 | 417 | 446 | 457 | 4% | −2% | −5% |
| 462 | 425 | 473 | 492 | 8% | −2% | −6% |

TABLE 10

In Vivo Sequential RCV on 3 Successive Days by Four Methods

| RCV (mL) | | | | % Difference vs $^{51}$Cr | | |
|---|---|---|---|---|---|---|
| $^{51}$Cr | $^{14}$C | Biotin | FACS | $^{14}$C | Biotin | FACS |
| 979 | 938 | 994 | 994 | 4% | −2% | −2% |
| 952 | 903 | 880 | 917 | 5% | 8% | 4% |
| 1013 | 934 | 1025 | 1030 | 8% | −1% | −2% |

EXAMPLE X

Initial Study to Establish Absence of Bacterial Contamination, Pyrogens, and of Neo-Antigens 1. Summary of Experimental Design and Results We have done an experiment using blood from five subjects to test whether the biotin labeled preparation (infusate) is pyrogen free, sterile and free of neo-antigens. This experiment was done to demonstrate the safety characteristics of the process for biotinylating red cells; none of the 5 batches of biotinylated red cells were reinfused into the volunteer donors. In order to assess sterility, the biotinylated red cells were cultured at the point that they would have been infused back into the donors (adult volunteers).

In order to assess whether bacterial contamination could have occurred during the process of blood drawing per se rather than during the biotinylation process, blood was also cultured immediately after drawing. Blood samples from the 5 subjects were sterile at the time of blood drawing and the biotinylated red cells from each of the 5 subjects were also sterile at the end of the biotinylation and washing process. Details are provided below.

In order to ascertain whether pyrogens were introduced by the process of biotinylation, the limulus lysate method (Pyrotell-T) was used to assay for the presence of pyrogens. As described in detail below, there was no evidence of pyrogens in the infusate buffer. The infusate buffer is the solution in which the biotinylated red cells are suspended immediately prior to reinfusion into the donor subject. In this initial study, the red cells were not infused.

In order to determine whether the process of biotinylation caused or unmasked neoantigens on the red cells, standard direct and indirect screening was done using a panel of sera as described in detail below. No neoantigens were detected.

2. Detailed Experimental Design:

Blood Collection:

Blood was drawn from each of five subjects. Individuals with type O blood were selected in order to avoid confounding the neoantigen screen with ABO incompatibility. The skin surface at the vein puncture site was cleaned with betadine and alcohol to insure sterility. 10 mL was drawn from each subject into a sterile syringe with no anticoagulant and 110 mL drawn into heparin (10 units/mL) syringes.

Sterility Testing:

Five mL of blood without anticoagulant was added to Bac-Tec bottles for culture. The bottle tops were cleaned with alcohol before injection of the blood from a syringe. The bottles were then taken to the clinical lab where they were monitored for growth for five days as per usual protocol. After biotin labeling (see section below), 5 mL of the labeled blood was added to separate Bac-Tec bottles for culture. The bottles were then taken to the clinical lab where they were monitored for five days.

Neo-Antigen Testing:

Five mL of the non-anticoagulated blood was drawn into EDTA vacutainers for neo-antigen testing. Samples were sent by Federal Express, on ice, to Dr. Ron Strauss at the University of Iowa, DeGowin Blood Center for this testing.

1) Three sets of red cells were prepared from each of the five subjects: one set consisted of normal blood in EDTA anticoagulant; the second set consisted of biotinylated red cells in saline wash solution; the third set consisted of biotinylated red cells in autologous plasma.

2) Upon arrival in Iowa City, red cells were washed in normal saline and adjusted to an hematocrit of 4 to 5%. Plasma from six normal individuals was selected to interact with the biotinylated red cells from the five subjects: three plasma were from three adults (presumably containing natural antibodies that would interact with exposed crypt- or neo-antigens); three plasma were from three umbilical cord samples (presumed not to contain natural antibodies).

3) Reaction mixtures were set up in which red cells from each of the five subjects were mixed individually with each of the six plasmas. One drop of red cells was incubated with two drops of plasma at 37° for 15 minutes. After incubation, reaction mixtures were observed for the presence of hemolysis and/or agglutination. Red cells in the reaction mixtures were then washed several times and anti-human antiglobulin serum (anti-IgG) was added. Again, the reaction mixtures were observed for the presence of hemolysis and/or agglutination. Finally, red cells coated with IgG (check cells) were added as a positive control to document the presence and activity of the antiglobulin serum; these positive controls showed the expected hemolysis and agglutination. All reactions using biotinylated red cells were negative (i.e., there was never evidence of either hemolysis or agglutination with any mixture of biotinylated red cells and plasma).

In order to screen even more sensitively for the binding of IgM and or compliment to the biotinylated red cells, the incubation and monitoring for hemolysis and/or agglutination described in 3) above were repeated using a broad spectrum anti-human globulin serum. There was no evidence of hemolysis or agglutination with any mixture of the biotinylated red cells and plasma.

Aseptic approach:

Labeling was done in sterile blood bags and all openings of vessels and transfers of fluids from one vessel to another were conducted in a class II, laminar flow hood using aseptic technique. All transfers were done using sterile syringes or sterile pipette tips. Procedures performed outside the hood are limited to vessels that were sealed or capped in the hood; these procedures include centrifugation and incubation in a dry incubator. All washing and liquid transfer processes were done in a Class II sterile hood to insure sterility.

Biotin Labeling of Red Cells:

100 mL of the heparinized blood was processed through 3 prewashes (4:1 ratio of wash solution volume to red cell volume). Biotinylating agent was added to give a ratio of 0.04 mg of sulfo-NHS-Biotin per mL packed red cells. After incubation at 25° C. for 60 minutes, the biotinylated red cells were washed four times in wash solution (4:1 ratio of wash to red cells). This is the standard wash/label/wash regimen for our labeling method.

Individual Component Preparation:

1) The sterile wash solution was prepared by adding 8 mL 50% Glucose, 20 mL 8.4% Sodium Bicarbonate and 1 mL Sodium Phosphates to 1 L of normal saline. Each of the component solutions were commercially available sterile preparations that are "pyrogen free" and "for injection". The final pH was 7.3, and the final concentrations were 149.7 mM NaCl, 21.5 mM Glucose, 19.4 mM $NaHCO_3$, 0.13 mM $NaH_2PO_4$, and 0.065 mM $Na_2HPO_4$.

2) The biotinylating solution was made by dissolving up to 0.04 mg/mL of the biotinylating agent sulfo-N-hydroxy-succinimide-biotin (Pierce Chemicals) in this wash solution; the biotinylating solution was then filtered sterilized using a 0.22 micron syringe filter.

Pyrogen Testing:

The products tested were the wash solution and the cell supernatant from the post washed red cells ready for infusion.

The method employed for pyrogen assay was Limulus Amebocyte Lysate Pyrotell-T Method (Associates of Cape Cod, Inc.). This is a flocculation test in which the endpoint is an increase in optical density. The endpoint method was employed. Reagents used from Associates of Cape Cod, Inc. were as follows: Pyrotell-T (lot # 42-122-564-T), LAL Reconstitution Buffer (Pyrosol) (lot # 226-70), LAL Reagent Water (pyrogen free water) (lot # 308-45). USP Reference Standard Endotoxin (RSE; lot F) was from U.S. Pharmacopoeia.

All work was performed under a class II hood until incubation. All dilutions and transfers were done using either sterile syringes or sterile pipette tips to deliver volumes.

The RSE (10,000 units/vial) was reconstituted in 2 mL of pyrogen free water delivered into the vial with a standardized pipette and sterile pipette tip. The rubber stopper was discarded and the vial capped with parafilm (the paper side is sterile and pyrogen free). Dissolution was allowed to proceed for 30 minutes with repeated shaking of the vial. 100 ul of this solution (delivered with a pipettor and sterile pipette tips) was diluted with 900 µl of pyrogen free water. Further dilutions were performed as shown below. Dilutions were done in 12×75 mm disposable glass tubes which were previously wrapped in aluminum foil and baked at 485° C. for 1 hour to sterilize and remove endotoxin contamination. Tubes were covered with parafilm after dilution to prevent contamination until solutions were transferred to the assay plate.

TABLE 11

| | Dilution of Endotoxin Standard Preparation of Standard Curve | | | | |
|---|---|---|---|---|---|
| RSE | 5,000 | EU/mL | | | |
| | µl CSE Dilution | µl pyrogen free water | Dilution | EU/mL | |
| | 100 | 900 | 10 | 500 | |
| | 100 | 900 | 10 | 50 | |
| | 100 | 900 | 10 | 5 | |
| | 400 | 1600 | 5 | 1 | |
| | 500 | 500 | 2 | 0.5 | |
| | 500 | 500 | 2 | 0.25 | Standard |
| | 500 | 500 | 2 | 0.125 | Curve |
| | 500 | 500 | 2 | 0.0625 | |
| | 500 | 500 | 2 | 0.03125 | |

As per Pyrotell T standard procedures, the positive control, (nominally 0.125 EU/mL), was prepared by dilution of the 1 EU/mL standard 1:8 with pyrogen free water. 600 µL of the 1 EU/mL standard was added to 4200 µL of pyrogen free water and capped with parafilm to prevent contamination.

The products (listed above) were diluted through a series of two 1:4 dilutions in 12×75 mm tubes. 500 µL of sample was added to 1500 mL of pyrogen free water and mixed. 500 µL of that dilution was then added to 1500 µL of pyrogen free water for the next dilution. Tubes were capped with parafilm to prevent contamination. Dilutions used for assay were 1, 4, 16×.

The vial of Pyrotell-T was reconstituted by addition of 5 mL of Pyrosol buffer from a sterile 5 mL syringe. The vial was then capped with parafilm to prevent contamination.

The assay was done in sterile, covered microtiter plates (Corning Cell Wells #25860). Negative controls contained 200 µL of pyrogen free water. Standards contained 100 µL of standard dilution plus 100 µL of pyrogen free water. Product tests contained 100 µL of product dilution plus 100 µL of pyrogen free water. "Positive product controls" contained 100 µL of product dilution plus 100 µL of a specific dilution of the control standard endotoxin (see discussion below). Finally, Pyrotell-T (45 µL) was added to each well. The final volume in each cell was 245 µL. The final reaction mixture was incubated for 45 minutes at 37° C. in a temperature controlled incubator. The plates were read on a Bio-Tek Plate Reader at 405 nm.

RESULTS

Sterility Testing:

Bac Tec bottles observed, by a registered Med-Tech in ACH Clinical Lab, both mechanically and visually.

TABLE 12

| Patent Identification | Labeling Period | Results |
|---|---|---|
| 1 | Pre | No growth at 5 days |
| 2 | Pre | No growth at 5 days |
| 3 | Pre | No growth at 5 days |
| 4 | Pre | No growth at 5 days |
| 5 | Pre | No growth at 5 days |
| 1 | Post | No growth at 5 days |
| 2 | Post | No growth at 5 days |

TABLE 12-continued

| Patent Identification | Labeling Period | Results |
| --- | --- | --- |
| 3 | Post | No growth at 5 days |
| 4 | Post | No growth at 5 days |
| 5 | Post | No growth at 5 days |

Pyrogen Test Data:

The average OD at 405 nm for duplicate samples was determined. The negative control is pyrogen free water; optical density (OD) was determined and subtracted from all other readings. The standard curve OD's were plotted against nominal standard concentrations (EU/mL), and a linear regression performed. The standard curve was linear with a correlation coefficient of 0.999 (exceeding the 0.980 coefficient required for validation of the assay). The y-intercept was an OD of 0.002, which is within acceptable experimental error of zero.

TABLE 13

| Patient Identification | Endotoxin EU/mL | Endotoxin Dose EU/kg | Positive Control Recovered |
| --- | --- | --- | --- |
| 1 | <0.031 | <0.043 | 61.65% |
| 2 | <0.031 | <0.043 | 78.54% |
| 3 | <0.031 | <0.043 | 71.24% |
| 4 | <0.031 | <0.043 | 74.43% |
| 5 | <0.031 | <0.043 | 75.35% |

Samples of the final suspension buffer for the biotinylated red cells from each subject were read against the standard curve to determine endotoxin concentrations. For each suspension buffer and all dilutions of each buffer, optical densities were less than zero (i.e., no detectable endotoxin over blank pyrogen free water). We conclude that all products tested were endotoxin free within the experimental parameters of the test. We calculated the maximum endotoxin exposure for the dose of suspension buffer (wash solution) of the labeled red cells given to each study subject. We based the maximum estimate on the sensitivity of the LAL assay (in our hands, as per standard LAL procedures). The maximum possible exposure was 0.043 EU/kg. This exposure is well below the endotoxin tolerance limit of 5 EU/kg set for parenterals as specified in the Limulus Amebocyte Lysate assay description and the FDA guideline.

Assay validity was further established by the correlation coefficient of the standard curve (as discussed above) and by the use of a "positive control" added to the product being tested. The logic here is that a standard amount of endotoxin is added to each of the products tested to assess the possibility that an individual "product" might interfere with the Limulus lysate assay and therefore mask the presence of endotoxin. The ideal response is to demonstrate complete recovery of the added known endotoxin. This approach is designated the "positive product control" in the terminology of Cape Cod Associates. The endotoxin of the positive product control was measured separately in the same assay. The acceptable range of recoveries is 100±50% of the added endotoxin. We tested positive product control at several dilutions of each of the products; our recoveries of the positive product control in each of the products was always within 100±50% and averaged 71.4% recovery.

CONCLUSIONS

We conclude that the labeling method, as described, using sterile, pyrogen-free wash solution, a class II hood, and sterile technique can produce a sterile, pyrogen free, and neoantigen free product.

The present invention is described with reference to certain preferred and alternative embodiments which are intended to be exemplary only and not by way of limitation to the full scope of the present invention as set forth in the appended claims.

What is claimed is:

1. A method for determining total circulating red blood cell volume (RCV) of a patient, comprising the sequential steps of:

(a) extracting a first volume of anticoagulated whole blood from said patent;

(b) separating red blood cells from said first volume of blood;

(c) washing said separated red blood cells four times with a 4:1 ratio of wash solution volume to separated red blood cell volume and sedimenting said washed red blood cells at 1500 x g for 10 minutes, wherein said wash solution comprises a phosphate buffered saline solutions with glucose;

(d) contacting said washed red blood cells with biotin to produce biotinylated red blood cells;

(e) reserving a first measured aliquot of said biotinylated red blood cells;

(f) diluting by a first measured dilution factor said first measured aliquot in a volume or unlabeled red blood cells from the patient to form a diluted standard sample of said biotinylated red blood cells;

(g) contacting said diluted standard sample with a biotin-binding label selected from the group consisting of fluorescein conjugated avidin, fluorescein conjugated streptavidin, radionuclide conjugated avidin and radionuclide conjugated streptavidin;

(h) separating free label from label bound to said biotinylated red blood cells in said diluted standard sample by dextran-metrizoic acid gradient centrifugation;

(i) measuring any label in said diluted standard sample to determine the concentration of bound label in said diluted sample;

(j) injecting a second measured volume of said biotinylated red blood cells back into said patient and allowing said biotinylated red blood cells to be diluted in and dispersed throughout said patient's total circulating red blood cell volume;

(k) extracting a second volume of anticoagulated whole blood from said patient;

(l) contacting said second volume of blood with a biotin-binding label selected from the group consisting of fluorescein conjugated avidin, fluorescein conjugated streptavidin, radionuclide conjugated avidin and radionuclide conjugated streptavidin;

(m) separating free label from label bound to said biotinylated red blood cells in said second volume of blood by dextran-metrizoic acid gradient centrifugation, whereby any red blood cells in said second volume agglutinate to form a pellet of red blood cells;

(n) measuring the packed cell volume of said pellet of red blood cells;

(o) measuring any label in said pellet to determine the concentration of bound label in said second volume of blood; and, (p) calculating said RCV of said patient according to the formula $$RCV = S*D*V_i/(B/H_v)$$

wherein

S is said concentration of label in said diluted standard sample measured in step (i), D is said dilution factor, $V_i$ is said measured volume of biotinylated red blood cells injected into said patient, B is said concentration of bound label in said second volume of blood measured in step (o), $H_v$ is said packed cell volume of said pellet,

* indicates the mathematical process of multiplication, and

/ indicates the mathematical process of division.

2. The method of claim 1 wherein said biotin-binding label is selected from the group consisting of fluorescein conjugated avidin and fluorescein conjugated streptavidin and further wherein said measuring of step (i) and step (o) is by fluorescence activated cell sorting.

3. The method of claim 1 wherein said biotin-binding label is selected from the group consisting of radionuclide conjugated avidin and radionuclide conjugated streptavidin wherein said radionuclide is $^{125}I$ and further wherein said measuring or step (i) and step (o) is by gamma counting.

4. The method of claim 1, comprising the additional step, subsequent to step (d), of adding lysine to said washed red blood cells to stop the biotinylation of said washed red blood cells.

5. The method of claim 4 wherein said biotin-binding label is selected from the group consisting of fluorescein conjugated avidin and fluorescein conjugated streptavidin and further wherein said measuring of step (i) and step (o) is by fluorescence activated cell sorting.

6. The method of claim 4 wherein said biotin-binding label is selected from the group consisting of radionuclide conjugated avidin and radionuclide conjugated streptavidin wherein said radionuclide is $^{125}I$ and further wherein said measuring of step (i) and step (o) is by gamma counting.

* * * * *